United States Patent
Gefen et al.

(10) Patent No.: US 8,718,784 B2
(45) Date of Patent: *May 6, 2014

(54) PENETRATING ELECTRODES FOR RETINAL STIMULATION

(75) Inventors: Ra'anan Gefen, Re'ut (IL); Rahul Saini, Plano, TX (US)

(73) Assignee: Nano-Retina, Inc., Wilmington, DE (US)

(*) Notice: Subject to any disclaimer, the term of this patent is extended or adjusted under 35 U.S.C. 154(b) by 680 days.

This patent is subject to a terminal disclaimer.

(21) Appl. No.: 12/687,509

(22) Filed: Jan. 14, 2010

(65) Prior Publication Data

US 2011/0172736 A1 Jul. 14, 2011

(51) Int. Cl.
*A61N 1/05* (2006.01)
(52) U.S. Cl.
USPC ............................................................ 607/54
(58) Field of Classification Search
USPC ............................................................ 607/53
See application file for complete search history.

(56) References Cited

U.S. PATENT DOCUMENTS

| | | |
|---|---|---|
| 1,662,446 A | 3/1928 | Wappler |
| 2,721,316 A | 10/1955 | Shaw |
| 2,760,483 A | 8/1956 | Tassicker |
| 4,551,149 A | 11/1985 | Sciarra |
| 4,601,545 A | 7/1986 | Kern |
| 4,628,933 A | 12/1986 | Michelson |
| 4,664,117 A | 5/1987 | Beck |
| 4,727,910 A | 3/1988 | Surkamp |
| 4,786,818 A | 11/1988 | Mead et al. |
| 4,837,049 A | 6/1989 | Byers et al. |
| 4,903,702 A | 2/1990 | Putz |
| 4,914,738 A | 4/1990 | Oda et al. |
| 4,969,468 A | 11/1990 | Byers et al. |
| 5,016,633 A | 5/1991 | Chow |
| 5,024,223 A | 6/1991 | Chow |
| 5,081,378 A | 1/1992 | Watanabe |
| 5,108,427 A | 4/1992 | Majercik et al. |
| 5,109,844 A | 5/1992 | de Juan, Jr. et al. |
| 5,133,356 A | 7/1992 | Bryan et al. |
| 5,147,284 A | 9/1992 | Fedorov et al. |
| 5,159,927 A | 11/1992 | Schmid |
| 5,215,088 A | 6/1993 | Normann et al. |

(Continued)

FOREIGN PATENT DOCUMENTS

| | | |
|---|---|---|
| WO | 01/91854 A1 | 12/2001 |
| WO | 03/032946 A2 | 4/2003 |

(Continued)

OTHER PUBLICATIONS

Tran et al. "A fully flexible stimulator using 65 nm CMOS process for 1024-electrode epi-retinal prosthesis." Conference Proceedings of the IEEE Engineering in Medicine and Biology Society. 2009;2009:1643-6.*

(Continued)

*Primary Examiner* — Luther Behringer

(57) ABSTRACT

Apparatus configured for implantation in a body of a subject is provided. The apparatus includes a support substrate, and at least 500 electrodes protruding at least 50 um from the support substrate, each electrode having (a) a distal tip, (b) an electrically-exposed tip portion, and (c) a cross-section of 50-1500 um2, 20 um from the distal tip. Other embodiments are also described.

19 Claims, 7 Drawing Sheets

(56) References Cited

U.S. PATENT DOCUMENTS

| | | |
|---|---|---|
| 5,397,350 A | 3/1995 | Chow et al. |
| 5,411,540 A | 5/1995 | Edell et al. |
| 5,476,494 A | 12/1995 | Edell et al. |
| 5,526,423 A | 6/1996 | Ohuchi et al. |
| 5,556,423 A | 9/1996 | Chow et al. |
| 5,575,813 A | 11/1996 | Edell et al. |
| 5,597,381 A | 1/1997 | Rizzo, III |
| 5,608,204 A | 3/1997 | Hofflinger et al. |
| 5,674,263 A | 10/1997 | Yamamoto et al. |
| 5,769,875 A | 6/1998 | Peckham et al. |
| 5,800,478 A | 9/1998 | Chen et al. |
| 5,800,533 A | 9/1998 | Eggleston et al. |
| 5,800,535 A | 9/1998 | Howard, III |
| 5,835,250 A | 11/1998 | Kanesaka |
| 5,836,996 A | 11/1998 | Doorish |
| 5,837,995 A | 11/1998 | Chow et al. |
| 5,865,839 A | 2/1999 | Doorish |
| 5,873,901 A | 2/1999 | Wu et al. |
| 5,895,415 A | 4/1999 | Chow et al. |
| 5,935,155 A | 8/1999 | Humayun et al. |
| 5,944,747 A | 8/1999 | Greenberg et al. |
| 5,949,064 A | 9/1999 | Chow et al. |
| 6,020,593 A | 2/2000 | Chow et al. |
| 6,032,062 A | 2/2000 | Nisch |
| 6,035,236 A | 3/2000 | Jarding et al. |
| 6,043,437 A | 3/2000 | Schulman et al. |
| 6,069,365 A | 5/2000 | Chow et al. |
| 6,075,251 A | 6/2000 | Chow et al. |
| 6,201,234 B1 | 3/2001 | Chow et al. |
| 6,230,057 B1 | 5/2001 | Chow et al. |
| 6,259,937 B1 | 7/2001 | Schulman et al. |
| 6,287,372 B1 | 9/2001 | Briand et al. |
| 6,298,270 B1 | 10/2001 | Nisch et al. |
| 6,324,429 B1 | 11/2001 | Shire et al. |
| 6,347,250 B1 | 2/2002 | Nisch et al. |
| 6,368,349 B1 | 4/2002 | Wyatt et al. |
| 6,389,317 B1 | 5/2002 | Chow et al. |
| 6,400,989 B1 | 6/2002 | Eckmiller |
| 6,427,087 B1 | 7/2002 | Chow et al. |
| 6,442,431 B1 | 8/2002 | Veraart et al. |
| 6,458,157 B1 | 10/2002 | Suaning |
| 6,472,122 B1 | 10/2002 | Schulman et al. |
| 6,473,365 B2 | 10/2002 | Joh et al. |
| 6,498,043 B1 | 12/2002 | Schulman et al. |
| 6,507,758 B1 | 1/2003 | Greenberg et al. |
| 6,533,798 B2 | 3/2003 | Greenberg et al. |
| 6,574,022 B2 | 6/2003 | Chow et al. |
| 6,611,716 B2 | 8/2003 | Chow et al. |
| 6,647,297 B2 | 11/2003 | Scribner |
| 6,658,299 B1 | 12/2003 | Dobelle |
| 6,677,225 B1 | 1/2004 | Ellis et al. |
| 6,678,458 B2 | 1/2004 | Ellis et al. |
| 6,683,645 B1 | 1/2004 | Collins et al. |
| 6,738,672 B2 | 5/2004 | Schulman et al. |
| 6,755,530 B1 | 6/2004 | Loftus et al. |
| 6,758,823 B2 | 7/2004 | Pasquale et al. |
| 6,761,724 B1 | 7/2004 | Zrenner et al. |
| 6,762,116 B1 | 7/2004 | Skidmore |
| 6,770,521 B2 | 8/2004 | Visokay et al. |
| 6,785,303 B1 | 8/2004 | Holzwarth et al. |
| 6,792,314 B2 | 9/2004 | Byers et al. |
| 6,804,560 B2 | 10/2004 | Nisch et al. |
| 6,821,154 B1 | 11/2004 | Canfield et al. |
| 6,844,023 B2 | 1/2005 | Schulman et al. |
| 6,847,847 B2 | 1/2005 | Nisch et al. |
| 6,888,571 B1 | 5/2005 | Koshizuka et al. |
| 6,904,239 B2 | 6/2005 | Chow et al. |
| 6,908,470 B2 | 6/2005 | Stieglitz et al. |
| 6,923,669 B1 | 8/2005 | Tsui et al. |
| 6,935,897 B2 | 8/2005 | Canfield et al. |
| 6,949,763 B2 | 9/2005 | Ovadia et al. |
| 6,961,619 B2 | 11/2005 | Casey |
| 6,970,745 B2 | 11/2005 | Scribner |
| 6,974,533 B2 | 12/2005 | Zhou |
| 6,976,998 B2 | 12/2005 | Rizzo et al. |
| 6,990,377 B2 | 1/2006 | Gliner et al. |
| 7,001,608 B2 | 2/2006 | Fishman et al. |
| 7,003,354 B2 | 2/2006 | Chow et al. |
| 7,006,873 B2 | 2/2006 | Chow et al. |
| 7,025,619 B2 | 4/2006 | Tsui et al. |
| 7,027,874 B1 | 4/2006 | Sawan et al. |
| 7,031,776 B2 | 4/2006 | Chow et al. |
| 7,035,692 B1 | 4/2006 | Maghribi et al. |
| 7,037,943 B2 | 5/2006 | Peyman |
| 7,047,080 B2 | 5/2006 | Palanker et al. |
| 7,058,455 B2 | 6/2006 | Huie, Jr. et al. |
| 7,071,546 B2 | 7/2006 | Fey et al. |
| 7,079,881 B2 | 7/2006 | Schulman et al. |
| 7,081,630 B2 | 7/2006 | Saini et al. |
| 7,096,568 B1 | 8/2006 | Nilsen et al. |
| 7,103,416 B2 | 9/2006 | Ok et al. |
| 7,107,097 B2 | 9/2006 | Stern et al. |
| 7,127,286 B2 | 10/2006 | Mech et al. |
| 7,127,301 B1 | 10/2006 | Okandan et al. |
| 7,130,693 B1 | 10/2006 | Montalbo |
| 7,133,724 B2 | 11/2006 | Greenberg et al. |
| 7,139,612 B2 | 11/2006 | Chow et al. |
| 7,147,865 B2 | 12/2006 | Fishman et al. |
| 7,149,586 B2 | 12/2006 | Greenberg et al. |
| 7,158,834 B2 | 1/2007 | Paul, Jr. |
| 7,158,836 B2 | 1/2007 | Suzuki |
| 7,160,672 B2 | 1/2007 | Schulman et al. |
| 7,162,308 B2 | 1/2007 | O'Brien et al. |
| 7,177,697 B2 | 2/2007 | Eckmiller et al. |
| 7,190,051 B2 | 3/2007 | Mech et al. |
| 7,191,010 B2 | 3/2007 | Ohta et al. |
| 7,224,300 B2 | 5/2007 | Dai et al. |
| 7,224,301 B2 | 5/2007 | Dai et al. |
| 7,235,350 B2 | 6/2007 | Schulman et al. |
| 7,242,597 B2 | 7/2007 | Shodo |
| 7,244,027 B2 | 7/2007 | Sumiya |
| 7,248,928 B2 | 7/2007 | Yagi |
| 7,251,528 B2 | 7/2007 | Harold |
| 7,255,871 B2 | 8/2007 | Huie, Jr. et al. |
| 7,257,446 B2 | 8/2007 | Greenberg et al. |
| 7,263,403 B2 | 8/2007 | Greenberg et al. |
| 7,271,525 B2 | 9/2007 | Byers et al. |
| 7,272,447 B2 | 9/2007 | Stett et al. |
| 7,291,540 B2 | 11/2007 | Mech et al. |
| 7,295,872 B2 | 11/2007 | Kelly et al. |
| 7,302,598 B2 | 11/2007 | Suzuki et al. |
| 7,314,474 B1 | 1/2008 | Greenberg et al. |
| 7,321,796 B2 | 1/2008 | Fink et al. |
| 7,342,427 B1 | 3/2008 | Fensore et al. |
| 7,377,646 B2 | 5/2008 | Suzuki |
| 7,379,000 B2 | 5/2008 | Dai et al. |
| 7,388,288 B2 | 6/2008 | Solzbacher et al. |
| 7,400,021 B2 | 7/2008 | Wu et al. |
| 7,447,547 B2 | 11/2008 | Palanker |
| 7,447,548 B2 | 11/2008 | Eckmiller |
| 7,480,988 B2 | 1/2009 | Ok et al. |
| 7,481,912 B2 | 1/2009 | Stelzle et al. |
| 7,482,957 B2 | 1/2009 | Dai et al. |
| 7,483,751 B2 | 1/2009 | Greenberg et al. |
| 7,493,169 B2 | 2/2009 | Greenberg et al. |
| 7,499,754 B2 | 3/2009 | Greenberg et al. |
| 7,539,544 B2 | 5/2009 | Greenberg et al. |
| 7,555,328 B2 | 6/2009 | Schulman et al. |
| 7,556,621 B2 | 7/2009 | Palanker et al. |
| 7,565,202 B2 | 7/2009 | Greenberg et al. |
| 7,565,203 B2 | 7/2009 | Greenberg et al. |
| 7,571,004 B2 | 8/2009 | Roy et al. |
| 7,571,011 B2 | 8/2009 | Zhou et al. |
| 7,574,263 B2 | 8/2009 | Greenberg et al. |
| 7,610,098 B2 | 10/2009 | McLean |
| 7,622,702 B2 | 11/2009 | Wu et al. |
| 7,630,771 B2 | 12/2009 | Cauller |
| 7,631,424 B2 | 12/2009 | Greenberg et al. |
| 7,638,032 B2 | 12/2009 | Zhou et al. |
| 7,666,523 B2 | 2/2010 | Zhou |
| 7,676,274 B2 | 3/2010 | Hung et al. |
| 7,691,252 B2 | 4/2010 | Zhou et al. |
| 7,706,887 B2 | 4/2010 | Tai et al. |
| 7,706,893 B2 | 4/2010 | Hung et al. |

(56) References Cited

U.S. PATENT DOCUMENTS

| | | |
|---|---|---|
| 7,709,961 B2 | 5/2010 | Greenberg et al. |
| 7,725,191 B2 | 5/2010 | Greenberg et al. |
| 7,734,352 B2 | 6/2010 | Greenberg et al. |
| 7,738,962 B2 | 6/2010 | Greenberg et al. |
| 7,749,608 B2 | 7/2010 | Laude et al. |
| 7,750,076 B2 | 7/2010 | Laude et al. |
| 7,751,896 B2 | 7/2010 | Graf et al. |
| 7,765,009 B2 | 7/2010 | Greenberg et al. |
| 7,766,903 B2 | 8/2010 | Blumenkranz et al. |
| 7,776,197 B2 | 8/2010 | Zhou |
| 7,831,309 B1 | 11/2010 | Humayun et al. |
| 7,834,767 B2 | 11/2010 | Shodo |
| 7,835,798 B2 | 11/2010 | Greenberg et al. |
| 7,840,273 B2 | 11/2010 | Schmid |
| 7,846,285 B2 | 12/2010 | Zhou et al. |
| 7,853,330 B2 | 12/2010 | Bradley et al. |
| 7,871,707 B2 | 1/2011 | Laude et al. |
| 7,877,866 B1 | 2/2011 | Greenberg et al. |
| 7,881,799 B2 | 2/2011 | Greenberg et al. |
| 7,887,681 B2 | 2/2011 | Zhou |
| 7,894,909 B2 | 2/2011 | Greenberg et al. |
| 7,894,911 B2 | 2/2011 | Greenberg et al. |
| 7,904,148 B2 | 3/2011 | Greenberg et al. |
| 7,908,011 B2 | 3/2011 | McMahon et al. |
| 7,912,556 B2 | 3/2011 | Greenberg et al. |
| 7,914,842 B1 | 3/2011 | Greenberg et al. |
| 7,937,153 B2 | 5/2011 | Zhou et al. |
| 7,957,811 B2 | 6/2011 | Caspi et al. |
| 7,962,221 B2 | 6/2011 | Greenberg et al. |
| 7,979,134 B2 | 7/2011 | Chow et al. |
| 7,989,080 B2 | 8/2011 | Greenberg et al. |
| 8,000,804 B1 | 8/2011 | Wessendorf et al. |
| 8,010,202 B2 | 8/2011 | Shah et al. |
| 8,010,206 B2 | 8/2011 | Dai et al. |
| 8,014,868 B2 | 9/2011 | Greenberg et al. |
| 8,014,869 B2 | 9/2011 | Greenberg et al. |
| 8,014,878 B2 | 9/2011 | Greenberg et al. |
| 8,024,022 B2* | 9/2011 | Schulman et al. ............ 600/372 |
| 8,034,229 B2 | 10/2011 | Zhou et al. |
| 8,046,078 B2 | 10/2011 | Greenberg et al. |
| 8,060,211 B2 | 11/2011 | Greenberg et al. |
| 8,060,216 B2 | 11/2011 | Greenberg et al. |
| 8,068,913 B2 | 11/2011 | Greenberg et al. |
| 8,078,284 B2 | 12/2011 | Greenberg et al. |
| 8,090,447 B2 | 1/2012 | Tano et al. |
| 8,090,448 B2 | 1/2012 | Greenberg et al. |
| 8,103,352 B2 | 1/2012 | Fried et al. |
| 8,121,697 B2 | 2/2012 | Greenberg et al. |
| 8,131,375 B2 | 3/2012 | Greenberg et al. |
| 8,131,378 B2 | 3/2012 | Greenberg et al. |
| 8,145,322 B1 | 3/2012 | Yao et al. |
| 8,150,526 B2* | 4/2012 | Gross et al. ............ 607/54 |
| 8,150,534 B2* | 4/2012 | Greenberg et al. ............ 607/116 |
| 8,160,713 B2 | 4/2012 | Greenberg et al. |
| 8,165,680 B2 | 4/2012 | Greenberg et al. |
| 8,170,676 B2 | 5/2012 | Greenberg et al. |
| 8,170,682 B2 | 5/2012 | Greenberg et al. |
| 8,180,453 B2 | 5/2012 | Greenberg et al. |
| 8,180,454 B2 | 5/2012 | Greenberg et al. |
| 8,180,460 B2 | 5/2012 | Nevsmith et al. |
| 8,190,267 B2 | 5/2012 | Greenberg et al. |
| 8,195,266 B2 | 6/2012 | Whalen, III et al. |
| 8,197,539 B2 | 6/2012 | Nasiatka et al. |
| 8,200,338 B2 | 6/2012 | Greenberg et al. |
| 8,226,661 B2 | 7/2012 | Balling et al. |
| 8,239,034 B2 | 8/2012 | Greenberg et al. |
| 8,244,362 B2 | 8/2012 | Yonezawa |
| 8,359,083 B2* | 1/2013 | Clark et al. ............ 600/378 |
| 2002/0091421 A1 | 7/2002 | Greenberg et al. |
| 2003/0023297 A1 | 1/2003 | Byers et al. |
| 2003/0032946 A1 | 2/2003 | Fishman et al. |
| 2003/0100823 A1* | 5/2003 | Kipke et al. ............ 600/378 |
| 2003/0208248 A1 | 11/2003 | Carter et al. |
| 2004/0054407 A1 | 3/2004 | Tashiro et al. |
| 2004/0078064 A1 | 4/2004 | Suzuki |
| 2004/0088026 A1 | 5/2004 | Chow et al. |
| 2004/0098067 A1 | 5/2004 | Ohta et al. |
| 2004/0181265 A1 | 9/2004 | Palanker et al. |
| 2004/0189940 A1 | 9/2004 | Kutschbach et al. |
| 2005/0015120 A1 | 1/2005 | Seibel et al. |
| 2005/0119605 A1 | 6/2005 | Sohn |
| 2005/0146954 A1 | 7/2005 | Win et al. |
| 2006/0106432 A1 | 5/2006 | Sawan et al. |
| 2006/0111757 A9 | 5/2006 | Greenberg et al. |
| 2006/0184245 A1 | 8/2006 | Graf et al. |
| 2006/0282128 A1 | 12/2006 | Tai et al. |
| 2006/0287688 A1 | 12/2006 | Yonezawa |
| 2007/0005116 A1 | 1/2007 | Lo |
| 2007/0123766 A1 | 5/2007 | Whalen, III et al. |
| 2007/0142877 A1 | 6/2007 | McLean |
| 2007/0142878 A1 | 6/2007 | Krulevitch et al. |
| 2007/0191909 A1 | 8/2007 | Ameri et al. |
| 2008/0114230 A1 | 5/2008 | Addis |
| 2008/0234791 A1 | 9/2008 | Arle et al. |
| 2008/0262571 A1 | 10/2008 | Greenberg et al. |
| 2008/0288036 A1 | 11/2008 | Greenberg et al. |
| 2009/0002034 A1 | 1/2009 | Westendorp et al. |
| 2009/0005835 A1 | 1/2009 | Greenberg et al. |
| 2009/0024182 A1 | 1/2009 | Zhang et al. |
| 2009/0118805 A1 | 5/2009 | Greenberg et al. |
| 2009/0192571 A1 | 7/2009 | Stett et al. |
| 2009/0204207 A1 | 8/2009 | Blum et al. |
| 2009/0204212 A1 | 8/2009 | Greenberg et al. |
| 2009/0216295 A1 | 8/2009 | Zrenner et al. |
| 2009/0228069 A1 | 9/2009 | Dai et al. |
| 2009/0287275 A1 | 11/2009 | Suaning et al. |
| 2009/0326623 A1 | 12/2009 | Greenberg et al. |
| 2010/0087895 A1 | 4/2010 | Zhou et al. |
| 2010/0204754 A1 | 8/2010 | Gross et al. |
| 2010/0249878 A1 | 9/2010 | McMahon et al. |
| 2010/0331682 A1 | 12/2010 | Stein et al. |
| 2011/0054583 A1 | 3/2011 | Litt et al. |
| 2011/0106229 A1* | 5/2011 | Ortmann ............ 607/116 |
| 2011/0172736 A1 | 7/2011 | Gefen et al. |
| 2012/0035725 A1* | 2/2012 | Gefen et al. ............ 623/6.22 |
| 2012/0035726 A1 | 2/2012 | Gross et al. |
| 2012/0041514 A1 | 2/2012 | Gross et al. |
| 2012/0209350 A1 | 8/2012 | Taylor et al. |
| 2012/0221103 A1 | 8/2012 | Liran et al. |
| 2012/0259410 A1 | 10/2012 | Gefen et al. |

FOREIGN PATENT DOCUMENTS

| | | |
|---|---|---|
| WO | 2007/009539 A2 | 1/2007 |
| WO | 2007/095395 A2 | 8/2007 |
| WO | 2010/035173 A1 | 4/2010 |
| WO | 2010/089739 A2 | 8/2010 |
| WO | 2011/086545 A2 | 7/2011 |
| WO | 2012/017426 A1 | 2/2012 |
| WO | 2012/114327 A2 | 8/2012 |
| WO | 2012/153325 A2 | 11/2012 |

OTHER PUBLICATIONS

USPTO OA mailed Aug. 24, 2011 in connection with U.S. Appl. No. 12/368,150.
International Search Report and Written Opinion PCT/IL11/00022 dated Aug. 12, 2011.
Eberhart Zrenner; "Will Retinal Implants Restore Vision?", Science, Feb. 8, 2002, vol. 295, pp. 1022-1025.
R.P.Jourdain, et al; "Fabrication of piezoelectric thick-film bimorph micro-actuators from bulk ceramics using batch-scale methods", Multi-Material Micro Manufacture, S. Dimov and W. Menz (Eds.) © 2008, Cardiff University, Cardiff, UK., Whittles Publishing Ltd. (Exact date not found).
C. Liang, et al; "Surface modification of cp-Ti using femtosecond laser micromachining and the deposition of Ca/P layer", Materials Letters, vol. 62, Issue 23, Aug. 31, 2008, pp. 3783-3786—abstract.
Jong-Mo Seo, et al; "Biocompatibility of polyimide microelectrode array for retinal stimulation", Materials Science & Engineering C, vol. 24, No. 1, Jan. 5, 2004, pp. 185-189.
Raya Sorkin, et al; "Process entanglement as a neuronal anchorage

(56) References Cited

OTHER PUBLICATIONS mechanism to rough surfaces", Nanotechnology 20 (2009), 015101, 8 pages, (Exact date not given).

Anatoliy Y. Vorobyev, et al; "Metallic Light Absorbers Produced by Femtosecond Laser Pulses", Hindawi Publishing Corporation, Advances in Mechanical Engineering, vol. 2010, Article ID 452749, 4 pages, doi:10.1155/2010/452749 (No Date Found).

A.Y. Vorobyev, et al; "Femtosecond laser structuring of titanium implants", Applied Surface Science, vol. 253, Issue 17, Jun. 30, 2007, pp. 7272-7280—Abstract.

Warren M Grill et al: "Implanted Neural Interfaces: Biochallenges and Engineered Solutions", Annu. Rev. Biomed. Eng. Mar. 31, 2009, 11 Abstract.

Warren M Grill, et al; "Implanted Neural Interfaces: Biochallenges and Engineered Solutions", Annu. Rev. Biomed. Eng. Mar. 31, 2009, 11: pp. 1-24.

Lars Wallman, et al; "The geometric design of micromachined silicon sieve electrodes influences functional nerve regeneration", Biomaterials, vol. 22, Issue 10, May 2001 (Exact date not found) pp. 1187-1193.

International Search Report: PCT/IL10/000097.

USPTO NFOA mailed Aug. 28, 2012 in connection with U.S. Appl. No. 12/852,218.

USPTO NFOA mailed Sep. 28, 2012 in connection with U.S. Appl. No. 13/103,264.

International Preliminary Report on Patentability dated Jul. 17, 2012 which issued during the prosecution of Appliant's PCT/IL2011/000022.

European Search Report dated Aug. 10, 2012; issued during prosecution of Applicant's European Application No. 10 73 8277.

ISR and Written Opinion dated Sep. 17, 2012 issued during the prosecution of Applicant's PCT/IL12/00057.

International Search Report dated Aug. 12, 2011 issued during the prosecution of Appliant's PCT/IL2011/000022.

Daniel Palanker, et al; "Design of a high-resolution optoelectronic retinal prosthesis", Journal of Neural Engineering, Institute of Physics Publishing, Bristol, GB. vol. 2, No. 1, Mar. 1, 2005, pp. S105-S120, XP002427333, ISSN: 1741-2552, DOI: 10.1088/1741-2560/2/1/012.

F.J. Pelayo, et al; "Cortical Visual Neuro-Prosthesis for the Blind: Retina-Like Software/Hardware Preprocessor", 2003 International IEEE/EMBS Conference on Neural Engineering-CNE; Mar. 20-22, 2003, pp. 150-153.

M. Schwarz, et al; "Single chip CMOS imagers and flexible microelectronic stimulators for a retina implant system", Sensors and Actuators; vol. 83, Issues 1-3 May 22, 2000, pp. 40-46.

International Search Report and Written Opinion dated Dec. 12, 2011 issued during the prosecution of Applicant's PCT/IL11/00609.

M. Schwarz, et al; "Hardware Architecture of a Neural Net Based Retina Implant for Patients Fuffering from Retinitis Pigmentosa", IEEE International Conference on Neural Networks, 1996. Jun. 3-6, 1996; vol. 2, pp. 653-658.

K. Ganesan, et al; "Diamond Penetrating Electrode Array for Epi-Retina Prosthesis", $32^{nd}$ Annual International Conference of the IEEE EMBS Buenos Aires, Argentina, Aug. 31-Sep. 4, 2010, pp. 6757-6760.

Warren M. Grill, et al; "Implanted Neural Interfaces: Biochallenges and Engineered Solutions", Annu. Rev. Biomed. Eng. 2009. vol. 11, pp. 1-24; First published online as a Review in Advance on Mar. 31, 2009.

Andreas G. Andreou, et al; "Translinear Circuits in Subthreshold MOS", Analog Integrated Circuits and Signal Processing an International Journal, vol. 9, No. 2, Mar. 1996, pp. 141-166.

Dr. Warren E. Finn, et al; "An Amphibian Model for Developing and Evaluating Retinal Prostheses", $18^{th}$ Annual International Conference of the IEEE Engineering in Medicine and Biology Society, Amsterdam 5.8.2: Voice and Neuroprosthetic Augmentation, Oct. 31-Nov. 3, 1996, pp. 1540-1541; vol. 4.

Shawn Kevin Kelly; "A System for Electrical Retinal Stimulation for Human Trials", Publisher: Massachusetts Institute of Technology; Jun. 1998, 45 pages.

Mark S. Humayun, et al; "Visual perception in a blind subject with a chronic microelectronic retinal prothesis", Vision Research, vol. 43, pp. 2573-2581, Nov. 2003.

Peter Walter, et al; "Cortical Activation Via an Implanted Wireless Retinal Prosthesis", Investigative Ophthalmology & Visual Science, May 2005, vol. 46, No. 5, pp. 1780-1785.

USPTO NFOA mailed Dec. 14, 2012 in connection with U.S. Appl. No. 13/034,516.

USPTO NFOA mailed Mar. 13, 2013 in connection with U.S. Appl. No. 13/148,461.

International Search Report dated Sep. 4, 2012; PCT/IL2012/000186.

Richard A Normann, et al; "High-resolution spatio-temporal mapping of visual pathways using multi-electrode arrays", Vision Research, vol. 41, Issues 10-11, pp. 1261-1275, May 2001.

Je-Min Yoo, et al; "Excimer laser deinsulaltion of Parylene-C on iridium for use in an activated iridium oxide film-coated Utah electrode array", Journal of Neuroscience Methods, vol. 215, pp. 78-87, Epub Feb. 28, 2013.

Extended European Search Report dated Jul. 16, 2003; Appln. 11732733.8-1652/2523598 PCT/IL2011000022.

Official Action, dated Oct. 22, 2013, which issued during the prosecution of U.S. Appl. No. 13/148,461.

Extended European Search Report dated Nov. 19, 2013 which issued during the prosecution of European Patent Application No. 11814197.7.

J.F. Rizzo, "Methods and Perceptual Thresholds for Short-Term Electrical Stimulation of Human Retina with Microelectrode Arrays", Investigative Ophthalmology and Visual Science, vol. 44, No. 12, (Dec. 1, 2003) pp. 5355-5361.

\* cited by examiner

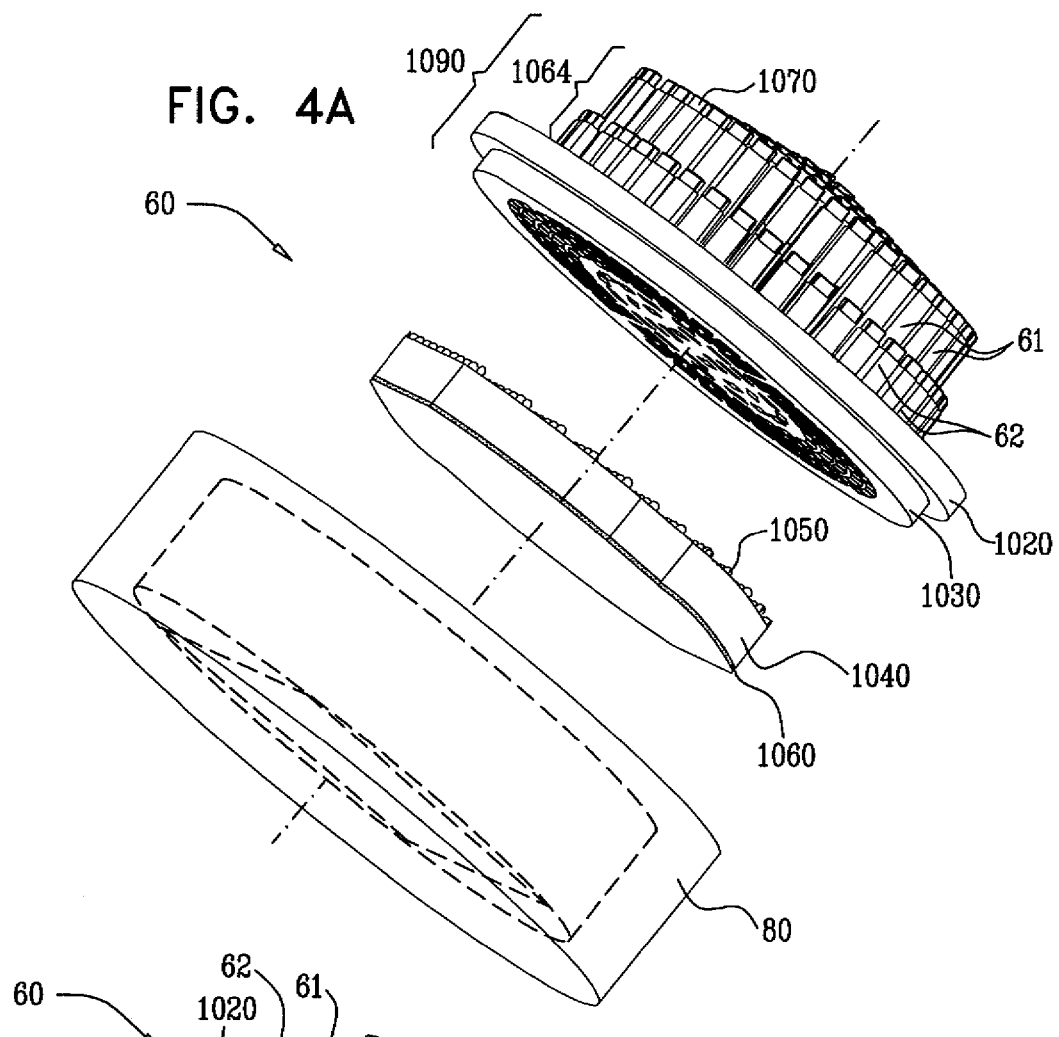
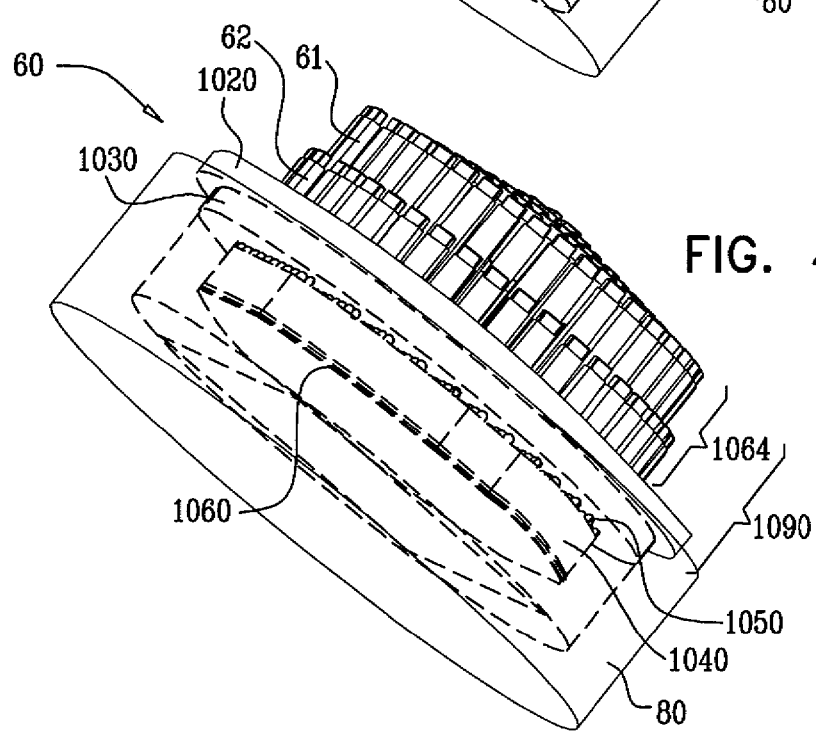

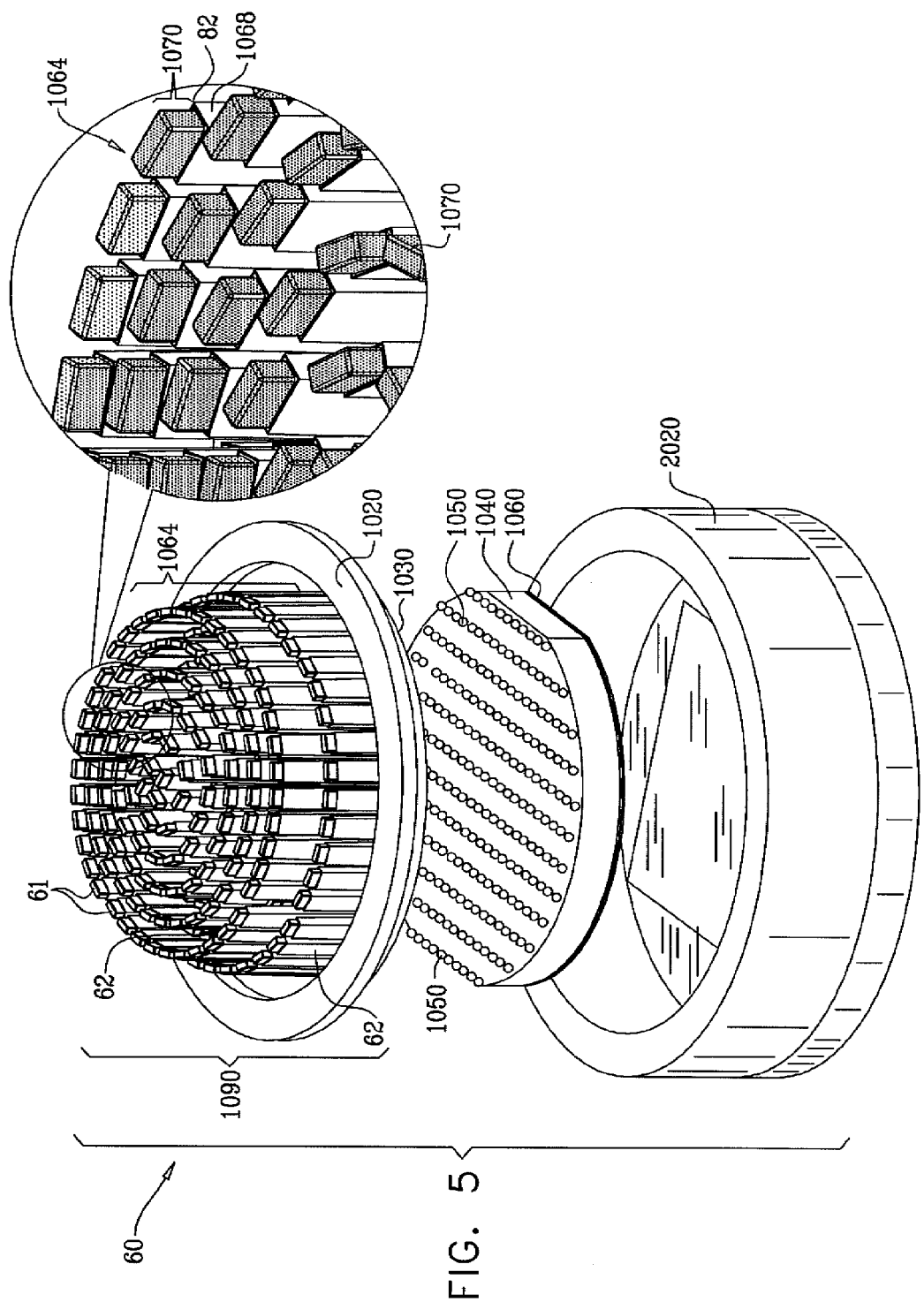

PENETRATING ELECTRODES FOR RETINAL STIMULATION

FIELD OF EMBODIMENTS OF THE INVENTION

Some applications of the invention relate generally to implantable medical devices and more specifically to a retinal electrode assembly.

BACKGROUND

Retinal malfunction, due to degenerative retinal diseases, is a leading cause of blindness and visual impairment. Implantation of a retinal prosthesis is a technology for restoring some useful vision in individuals suffering from retinal-related blindness.

The retina is a multi-layered light-sensitive structure that lines the posterior, inner part of the eye. The retina contains photoreceptor cells, for example rods and cones, which capture light and convert light signals into neural signals transmitted through the optic nerve to the brain. A bipolar cell layer exists between the photoreceptors and ganglion cells of the retina. The bipolar cell layer transmits signals from the photoreceptors to the ganglion cells whose axons form the optic nerve and transmit visual information to the brain.

Grill W., et al. describe in an article, entitled "Implanted Neural Interfaces: Biochallenges and Engineered Solutions," Annu. Rev. Biomed. Eng. 2009. 11:1-24, a regenerative sieve electrode that has holes to allow processes from a severed neuron to grow through. The article includes a schematic illustration of a sieve electrode.

U.S. Pat. No. 6,908,470 to Stieglitz describes a sieve electrode for connection to a nerve stump, which is composed of a thin flexible substrate with a plurality of ports for nerve filaments and several electrodes that are disposed on at least some of said ports on said substrate and adapted for being electrically contacted via conductors on said substrate, as well as of at least one counter-electrode. The substrate presents tabs protruding from the edge for fixing the substrate on a face of the nerve stump, which serve, at the same time, as carrier of the counter electrode. With this sieve electrode a neuro-technological interface is provided that is described as permitting a low-lesion contact with the nerve stump at a maximum of useable surface for the ports.

U.S. Pat. No. 4,969,468 to Byers describes an electrode array device for making multiple electrical contacts with cellular tissue or organs. The electrode array includes a base, a two dimensional array of conducting protuberances arising from the base and serving as electrodes, and conductors embedded onto the base and connected to such protuberances for transmitting electrical signals to and/or from the protuberances. The protuberances may also include an insulating layer which covers either the entire protuberance or which leaves the tips exposed for making focused electrical contact. Electrode arrays may be used singly or in combination with a second electrode array so as to form a sandwich around a target tissue. The sandwich electrode array may employ indexing cones for aligning the opposing electrode arrays and for limiting their vertical proximity. The conductors of the electrode array may be electronically connected or coupled to processing circuitry which amplifies and analyzes the signal received from the tissue and/or which generates signals which are sent to the target tissue and possibly coordinates the generated signals with signals which originate with the tissue.

The following patents and patent application publications may be of interest:

| | |
|---|---|
| U.S. Pat. No. 5,109,844 | U.S. Pat. No. 1,662,446 |
| U.S. Pat. No. 5,133,356 | U.S. Pat. No. 2,721,316 |
| U.S. Pat. No. 5,147,284 | U.S. Pat. No. 2,760,483 |
| U.S. Pat. No. 5,159,927 | U.S. Pat. No. 4,272,910 |
| U.S. Pat. No. 5,397,350 | U.S. Pat. No. 4,551,149 |
| U.S. Pat. No. 5,411,540 | U.S. Pat. No. 4,601,545 |
| U.S. Pat. No. 5,476,494 | U.S. Pat. No. 4,628,933 |
| U.S. Pat. No. 5,526,423 | U.S. Pat. No. 4,664,117 |
| U.S. Pat. No. 5,575,813 | U.S. Pat. No. 4,837,049 |
| U.S. Pat. No. 5,674,263 | U.S. Pat. No. 4,903,702 |
| U.S. Pat. No. 5,575,813 | U.S. Pat. No. 5,016,633 |
| U.S. Pat. No. 5,800,533 | U.S. Pat. No. 5,024,223 |
| U.S. Pat. No. 5,800,535 | U.S. Pat. No. 5,108,427 |
| U.S. Pat. No. 6,923,669 | U.S. Pat. No. 5,836,996 |
| U.S. Pat. No. 7,003,354 | U.S. Pat. No. 5,837,995 |
| U.S. Pat. No. 7,006,873 | U.S. Pat. No. 5,865,839 |
| U.S. Pat. No. 7,025,619 | U.S. Pat. No. 5,873,901 |
| U.S. Pat. No. 7,027,874 | U.S. Pat. No. 5,895,415 |
| U.S. Pat. No. 7,031,776 | U.S. Pat. No. 5,944,747 |
| U.S. Pat. No. 7,037,943 | U.S. Pat. No. 6,032,062 |
| U.S. Pat. No. 7,047,080 | U.S. Pat. No. 6,230,057 |
| U.S. Pat. No. 7,081,630 | U.S. Pat. No. 6,298,270 |
| U.S. Pat. No. 7,096,568 | U.S. Pat. No. 6,389,317 |
| U.S. Pat. No. 7,103,416 | U.S. Pat. No. 6,442,431 |
| U.S. Pat. No. 7,107,097 | U.S. Pat. No. 6,473,365 |
| U.S. Pat. No. 7,139,612 | U.S. Pat. No. 6,611,716 |
| U.S. Pat. No. 7,162,308 | U.S. Pat. No. 6,658,299 |
| U.S. Pat. No. 7,251,528 | U.S. Pat. No. 6,677,225 |
| U.S. Pat. No. 7,321,796 | U.S. Pat. No. 6,678,458 |
| PCT WO 2003/32946 | U.S. Pat. No. 6,755,530 |
| PCT WO 2001/91854 | U.S. Pat. No. 6,762,116 |
| PCT WO 2007/09539 | U.S. Pat. No. 6,770,521 |

The following articles, which are incorporated herein by reference, may be of interest:

Jourdain R P., et al., "Fabrication of piezoelectric thick-film bimorph micro-actuators from bulk ceramics using batch-scale methods" Multi-Material Micro Manufacture, S. Dimov and W. Menz (Eds.) 2008 Cardiff University, Cardiff, UK., Whittles Publishing Ltd.

Lianga C, et al., "Surface modification of cp-Ti using femtosecond laser micromachining and the deposition of Ca/P layer" Materials Letters Volume 62, Issue 23, 31 Aug. 2008, Pages 3783-3786.

Seo J M., et al., "Biocompatibility of polyimide microelectrode array for retinal stimulation," Materials Science and Engineering: C, Volume 24, Number 1, 5 Jan. 2004, pp. 185-189(5)"

Sorkin R., et al., "Process entanglement as a neuronal anchorage mechanism to rough surfaces," Nanotechnology 20 (2009) 015101 (8pp)

Vorobyeva A Y. et al., "Metallic light absorbers produced by femtosecond laser pulses," Advances in Mechanical Engineering, Volume 2010, Article ID 452749, 4 pages doi:10.1155/2010/452749

Vorobyeva A Y. et al., "Femtosecond laser structuring of titanium implants," Applied Surface Science, Volume 253, Issue 17, 30 Jun. 2007, Pages 7272-7280.

Wallman L., et al., "The geometric design of micromachined silicon sieve electrodes influences functional nerve regeneration," Biomaterials 2001 May:22(10):1187-93

Zrenner E., 2002, "Will retinal implants restore vision?" Science 295(5557), pp. 1022-5.

SUMMARY OF EMBODIMENTS OF THE INVENTION

In some applications of the present invention, implantable intraocular apparatus is provided for stimulating a retina of a subject suffering from a retinal disease and restoring at least partial vision in the subject.

The intraocular apparatus, which is implanted entirely in the subject's eye, typically comprises an intraocular retinal prosthesis, configured to be implanted in the subject's eye in either an epi-retinal or a sub-retinal position.

The apparatus typically comprises a support substrate and an array of electrodes protruding from the support substrate. (In this context, in the specification and in the claims, "array" is meant to include rectangular as well as non-rectangular arrays (such as circular arrays). The protruding electrodes are shaped to define electrically-exposed tips which penetrate retinal tissue of the subject, bringing the electrodes in contact with the tissue. For some applications, a surface of the electrodes is treated to increase roughness and surface area of the electrodes, thus reducing electrode impendence and facilitating retinal stimulation and/or axon regeneration. Additionally or alternatively, the exposed tips of the electrodes have perforations passing therethrough, further increasing the surface area of the electrodes and allowing neuronal processes, to pass through and intertwine with the electrodes.

For some applications, the support substrate from which the electrodes protrude comprises additional elements of a retinal prosthesis, e.g., an energy receiving layer, a photosensor layer and driving circuitry that is powered by the energy receiving layer. The driving circuitry typically drives current into the retinal tissue from the perforated rough tips of the electrodes, in response to sensing by the photosensor layer, in order to stimulate the retinal tissue.

The inventors have identified that, for some applications, sufficient stimulation of retinal tissue is a characteristic for consideration in enabling proper function of a retinal prosthesis. In particular, facilitating stimulation of the bipolar cell layer of the retina, which in turn stimulates ganglion cells, is a characteristic for consideration in retinal prosthesis provided by some applications of the present invention. The ganglion cells, whose axons form the optic nerve, further transmit the visual information to the brain resulting in the formation of an image. Penetrating perforated electrodes, in contrast to surface electrodes known in the art which sit on the surface of tissue, are configured to extend from either an epi-retinal or a sub-retinal implantation site and penetrate retinal tissue to directly contact and drive current into the bipolar cell layer from typically less than 10 um from the nearest bipolar cell. Rough electrode surfaces and perforations passing through the electrodes allow neuronal processes to grow therethrough, further improving cell-electrode coupling and increasing stimulation. Increased and direct contact of the retinal tissue by penetrating perforated electrodes enhances stimulation of the retina resulting in enhanced image resolution.

There is therefore provided, in accordance with some applications of the present invention, apparatus configured for implantation in a body of a subject, including:
a support substrate; and
at least 500 electrodes protruding at least 50 um from the support substrate, each electrode having (a) a distal tip, (b) an electrically-exposed tip portion, and (c) a cross-section of 50-1500 um2, 20 um from the distal tip.

In some applications, each electrode has a cross section of at least 200 um2, 20 um from the distal tip.

In some applications, the at least 500 electrodes include 1000-3000 electrodes.

In some applications, the at least 500 electrodes include 3000-6000 electrodes.

In some applications, a spatial density of the electrodes is 50-400 electrodes per mm2.

In some applications, the electrodes protrude perpendicularly from the support substrate.

In some applications, each electrode tip has a rough surface.

In some applications, the rough surface has a surface area that is increased by a factor of more than 50 due to being rough.

In some applications, some area of the tips of the electrodes are coated with carbon nanotubes.

In some applications, the apparatus is configured for implantation in an eye of the subject.

In some applications, the eye of the subject includes retinal tissue of the subject, and the tips are configured to penetrate the retinal tissue.

In some applications, the retinal tissue of the subject includes a retinal bipolar cell layer of the subject, and the tips are configured to penetrate the retinal bipolar cell layer.

In some applications, the tissue of the subject includes a retinal ganglion cell layer of the subject, and the tips are configured to penetrate the retinal ganglion cell layer.

In some applications, the electrodes include silicon.

In some applications, the electrodes include titanium.

In some applications, the electrodes include palladium.

In some applications, the electrically-exposed tip portion of each electrode is 25-100 um in length.

In some applications, each electrode includes an electrically-insulated body portion, proximal to the electrically-exposed tip.

In some applications, the electrically-insulated body portion has a length of 75-200 um.

In some applications, the electrically-insulated body portion has a length of 200-700 um.

In some applications, the electrically-insulated body portion has a length of 100-650 um.

In some applications, the electrically-insulated body portion includes an elliptical base portion at a proximal end of the body portion.

In some applications, the elliptical base portion has a major axis of 50-150 um and a minor axis of 25-80 um, the major axis being at least two times longer than the minor axis.

In some applications, the electrically-exposed tip portion of each electrode has an area of at least 750 um2.

In some applications, a cross-sectional area of each electrode declines monotonically from (a) a point 50 um from the distal tip to (b) the distal tip.

In some applications, the electrically-exposed tip portion of each electrode has a width of 15-60 um at a point 50 um from the distal tip.

In some applications, the electrically-exposed tip portion of each electrode has a width of 1-20 um at a point 4 um from the distal tip.

In some applications, the electrically-exposed tip portion of each electrode has a thickness of 5-20 um at a point 50 um from the distal tip.

In some applications, the electrically-exposed tip portion of each electrode has a thickness of 0.5-5 um at a point 4 um from the distal tip.

In some applications, each distal tip has a radius of curvature of 0.5-5 um.

In some applications, the radius of curvature of the distal tips is 1-3 um.

In some applications, a distance from the substrate to the distal tip of each electrode is 200-500 um.

In some applications, the distal tip of the tips of the electrodes have an average distance from the support substrate of 20-150 um.

In some applications, the support substrate includes an energy receiving layer and a photosensor layer, and the apparatus further includes driving circuitry that is powered by the energy receiving layer and drives current into the tissue from the tips of the electrodes, in response to sensing by the photosensor layer.

In some applications, the electrically-exposed tip portion of each electrode is shaped to define a hook configured to penetrate the tissue of the subject and anchor to the tissue.

In some applications, the support substrate is generally flexible.

In some applications, the flexible support substrate is bent during implantation of the apparatus in order to match a natural curvature of a retina of the subject.

In some applications, the tips of the electrodes together define a convex curved surface having a radius of curvature that is 6-15 mm.

In some applications, the apparatus includes at least 100 surface electrodes, and the protruding electrodes are shaped to define respective tips having rough surfaces and configured for penetrating tissue of the subject.

In some applications, the surface electrodes are configured to function as return electrodes.

In some applications, the at least 500 electrodes are arranged in at least 10 clusters of three or more electrodes, the distal tips being configured for penetrating tissue of the subject, and:

at least some of the electrodes in each cluster are configured to drive respective currents into the tissue of the subject, and the current driven by each electrode in the cluster is returned via an electrode in the cluster that serves as a common return electrode for the other electrodes in the cluster.

In some applications, at least some of the clusters include fewer than six electrodes.

In some applications, the at least 10 clusters include 100-500 clusters.

In some applications, the at least 10 clusters include 500-1500 clusters.

In some applications, the electrically-exposed tip portion of each electrode is shaped to define one or more perforations passing therethrough and is configured for penetrating tissue of the subject.

There is additionally provided, in accordance with some applications of the present invention apparatus configured for implantation in a body of a subject, the apparatus including:

a support substrate; and an array of at least 100 short electrodes and at least 400 long electrodes that are longer than the short electrodes, the short and long electrodes coupled to the support substrate and protruding at least 50 um from the support substrate, and shaped to define respective tips having rough surfaces and configured for penetrating tissue of the subject.

In some applications, the short electrodes are 150-550 um in length.

In some applications, the long electrodes are 300-700 um in length.

In some applications, the long electrodes are at least 50 um longer than adjacent short electrodes.

In some applications, the long electrodes are at least 150 um longer than adjacent short electrodes.

In some applications, the apparatus includes driving circuitry that is configured to drive current between respective ones of the long electrodes and respective ones of the short electrodes.

In some applications, the long and short electrodes are disposed on the support substrate in alternation.

In some applications, the long and short electrodes are disposed on the support substrate in alternating concentric rings.

In some applications, the support substrate includes an energy receiving layer and a photosensor layer, and the apparatus further includes driving circuitry that is powered by the energy receiving layer and drives current into the tissue from the tips of the electrodes, in response to sensing by the photosensor layer.

In some applications, the apparatus is configured for implantation in an eye of a subject.

In some applications, the tissue of the subject includes retinal tissue, and the long electrodes are configured to penetrate a retinal bipolar cell layer, and the short electrodes are configured to penetrate a retinal ganglion cell layer of the subject.

In some applications, the tissue of the subject includes retinal tissue, and the long electrodes are configured to penetrate a retinal bipolar cell layer, and the short electrodes are configured to penetrate a retinal Nuclear Fiber Layer of the subject.

In some applications, the apparatus includes a glass cap, which encapsulates the support substrate.

In some applications, the apparatus includes a metal ring surrounding the support substrate.

In some applications, the apparatus is flexible.

In some applications, the apparatus is rigid.

In some applications, the apparatus is configured to match a natural curvature of a retina of the subject.

In some applications, the tips of the electrodes together define a convex curved surface having a radius of curvature that is 6-15 mm.

There is further provided, in accordance with some applications of the present invention, apparatus configured for implantation in a body of a subject, including:

a support substrate; and an array of at least 100 surface electrodes and at least 400 protruding electrodes protruding from the support substrate, and the protruding electrodes shaped to define respective tips having rough surfaces and configured for penetrating tissue of the subject.

In some applications, the tissue includes retinal tissue of the subject and the protruding electrodes are configured to penetrate the retinal tissue of the subject.

In some applications, the protruding electrodes are 20-150 um in length.

In some applications, the protruding electrodes are 200-500 um in length.

In some applications, the surface electrodes project no more than 5 um from the support substrate.

In some applications, the apparatus includes driving circuitry that is configured to drive current into the tissue from the tips of the protruding electrodes.

In some applications, the surface electrodes are configured to function as return electrodes.

In some applications, the tips of the protruding electrodes together define a convex curved surface having a radius of curvature that is between 6-15 mm.

There is also provided, in accordance with some applications of the present invention, apparatus configured for implantation in a body of a subject, including:

a support substrate; and an array of at least 10 clusters of three or more electrodes, the electrodes protruding from the support substrate and shaped to define respective tips configured for penetrating tissue of the subject, and:

at least some of the electrodes in each cluster are configured to drive respective currents into the tissue of the subject, and the current driven by each electrode in the cluster is returned via an electrode in the cluster that serves as a common return electrode for the other electrodes in the cluster.

In some applications, at least some of the clusters include fewer than six electrodes.

In some applications, the at least 10 clusters include 100-500 clusters.

In some applications, the at least 10 clusters include 500-1500 clusters.

There is further yet provided in accordance with some applications of the present inventions, apparatus configured for implantation in a body of a subject, including:
  a support substrate; and
  an array of at least 500 electrodes coupled to the support substrate and protruding from the support substrate, and shaped to define respective tips configured for penetrating tissue of the subject, the tips of the electrodes together defining a convex curved surface having a radius of curvature that is between 6-15 mm.

In some applications, the electrodes protrude from the support substrate by at least 50 um.

There is yet additionally provided in accordance with applications of the present invention, apparatus configured for implantation in a body of a subject, including:
  a support substrate; and
  a plurality of electrodes protruding from the support substrate, each electrode having (a) a distal tip; and (b) an electrically-exposed tip portion that is shaped to define perforations passing therethrough and configured for penetrating tissue of the subject.

In some applications, each electrically-exposed tip portion has 1-50 perforations passing therethrough.

In some applications, the perforations have an average diameter of 2-10 um.

In some applications, each electrode electrically-exposed tip portion has a rough surface.

In some applications, the electrically-exposed tip portions of the electrodes are coated with carbon nanotubes In some applications, the plurality of electrodes includes at least 500 electrodes.

In some applications, the plurality of electrodes includes 1000-6000 electrodes.

In some applications, a spatial density of the electrodes is 50-400 electrodes per mm2.

In some applications, the electrodes protrude perpendicularly from the support substrate.

In some applications, in each electrode has a cross-section of at least 50 um2, 20 um from the distal tip.

In some applications, the cross-section is less than 1500 um2, 20 um from the distal tip.

In some applications, each electrode has a cross section of at least 200 um2, 20 um from the distal tip.

In some applications, the apparatus is configured for implantation in an eye of the subject.

In some applications, the tip of each electrically-exposed tip is 25-100 um in length.

In some applications, each electrode includes an electrically-insulated body portion, proximal to the electrically-exposed tip.

In some applications, the electrically-insulated body portion has a length of 25-200 um.

In some applications, the electrically-insulated body portion has a length of 200-700 um In some applications, the electrically-insulated body portion has a length of 100-650 um In some applications, the electrically-insulated body portion includes an elliptical base portion at a proximal end of the body portion.

In some applications, the elliptical base portion has a major axis of 50-150 um and a minor axis of 25-80 um, the major axis being at least two times longer than the minor axis.

In some applications, each electrode has an electrically-exposed area of at least 750 um2.

In some applications, a cross-sectional area of each electrode declines monotonically from (a) a point 50 um from the distal tip to (b) the distal tip.

In some applications, each distal tip has a radius of curvature of 0.5-5 um.

In some applications, a radius of curvature of the distal tips is 2 um.

In some applications, a distance from the substrate to the distal tip of each electrode is 50-500 um.

In some applications, the support substrate includes an energy receiving layer and a photosensor layer, and the apparatus further includes driving circuitry that is powered by the energy receiving layer and drives current into the tissue from the tips of the electrodes, in response to sensing by the photosensor layer.

In some applications, the tips of the electrodes together define a convex curved surface having a radius of curvature that is between 6-15 mm.

There is also additionally provided in accordance with some applications of the present invention, apparatus configured for implantation in a body of a subject, including:
  a support substrate; and
  at least 500 electrodes protruding from the support substrate, each electrode having (a) a distal tip; and (b) an electrically-exposed tip portion that has one or more perforations passing therethrough, the perforations having an average diameter of 2-10 um, the distal tips of the electrodes having an average distance from the support substrate of 100-300 um.

There is further yet provided in accordance with some applications of the present invention, a method for retinal stimulation including:
  identifying a subject as suffering from a retinal disease; and
  in response to identifying the subject, implanting in the subject's eye:
    a support substrate; and
    at least 500 electrodes protruding at least 50 um from the support substrate, each electrode having (a) a distal tip, (b) an electrically-exposed tip portion, and (c) a cross-section of 50-1500 um2, 20 um from the distal tip.

In some applications, each electrode has a cross section of at least 200 um2, 20 um from the distal tip.

There is also further additionally provided in accordance with some applications of the present invention, a method for retinal stimulation including:
  identifying a subject as suffering from a retinal disease; and
  in response to identifying the subject, implanting in the subject's eye:
    a support substrate; and
    an array of at least 100 short electrodes and at least 400 long electrodes that are longer than the short electrodes, the short and long electrodes coupled to the support substrate and protruding at least 50 um from the support substrate, and shaped to define respective tips having rough surfaces and configured for penetrating tissue of the subject.

There is also further provided in accordance with some applications of the present invention, a method for retinal stimulation including:
  identifying a subject as suffering from a retinal disease; and in response to identifying the subject, implanting in the subject's eye:
a support substrate; and
an array of at least 500 electrodes coupled to the support substrate and protruding from the support substrate, and shaped to define respective tips configured for penetrating tissue of the subject, the tips of the electrodes together defining a convex curved surface having a radius of curvature that is 6-15 mm.

There is still additionally provided in accordance with some applications of the present invention, a method for retinal stimulation including:
identifying a subject as suffering from a retinal disease; and
in response to identifying the subject, implanting in the subject's eye:
a support substrate; and
a plurality of electrodes protruding from the support substrate, the electrodes shaped to define respective pointed tips having perforations passing therethrough and configured for penetrating retinal tissue of the subject.

There is still yet provided in accordance with some applications of the present invention, a method for retinal stimulation including:
identifying a subject as suffering from a retinal disease; and
in response to identifying the subject, implanting in the subject's eye:
a support substrate; and
at least 500 electrodes protruding from the support substrate, each electrode having (a) a distal tip; and (b) an electrically-exposed tip portion that has one or more perforations passing therethrough, the perforations having an average diameter of 1-10 um, the distal tip of the electrodes having an average distance from the support substrate of 100-300 um.

There is still further provided in accordance with some applications of the present invention, a method for retinal stimulation including:
identifying a subject as suffering from a retinal disease; and
in response to identifying the subject, implanting in the subject's eye:
a support substrate; and
an array of at least 10 clusters of three or more electrodes, the electrodes protruding from the support substrate and shaped to define respective tips configured for penetrating tissue of the subject, and:
at least some of the electrodes in each cluster are configured to drive currents into the tissue of the subject, and
the current driven by each electrode in the cluster is returned via an electrode in the cluster that serves as a common return electrode for the other electrodes in the cluster.

There is further yet provided in accordance with some applications of the present invention, a method for stimulation of tissue, the method including:
identifying a subject as being suitable for tissue stimulation; and
in response to identifying the subject, implanting in the tissue of the subject:
a support substrate; and
at least 400 electrodes protruding at least 50 from the support substrate, each electrode having (a) a distal tip, (b) an electrically-exposed tip portion and (c) a cross-section of 50-1500 um2, 20 um from the distal tip.

In some applications, the tissue includes nervous tissue, and implanting includes implanting in the nervous tissue.

In some applications, each electrode has a cross-section of at least 200 um2, 20 um from the distal tip.

The present invention will be more fully understood from the following detailed description of applications thereof, taken together with the drawings, in which:

BRIEF DESCRIPTION OF THE DRAWINGS

FIGS. 4A-B are schematic illustrations of apparatus for retinal stimulation, in accordance with some applications of the present invention;

FIG. 5 is a schematic illustration of apparatus for retinal stimulation, in accordance with some applications of the present invention;

DETAILED DESCRIPTION OF EMBODIMENTS

Figure 1:
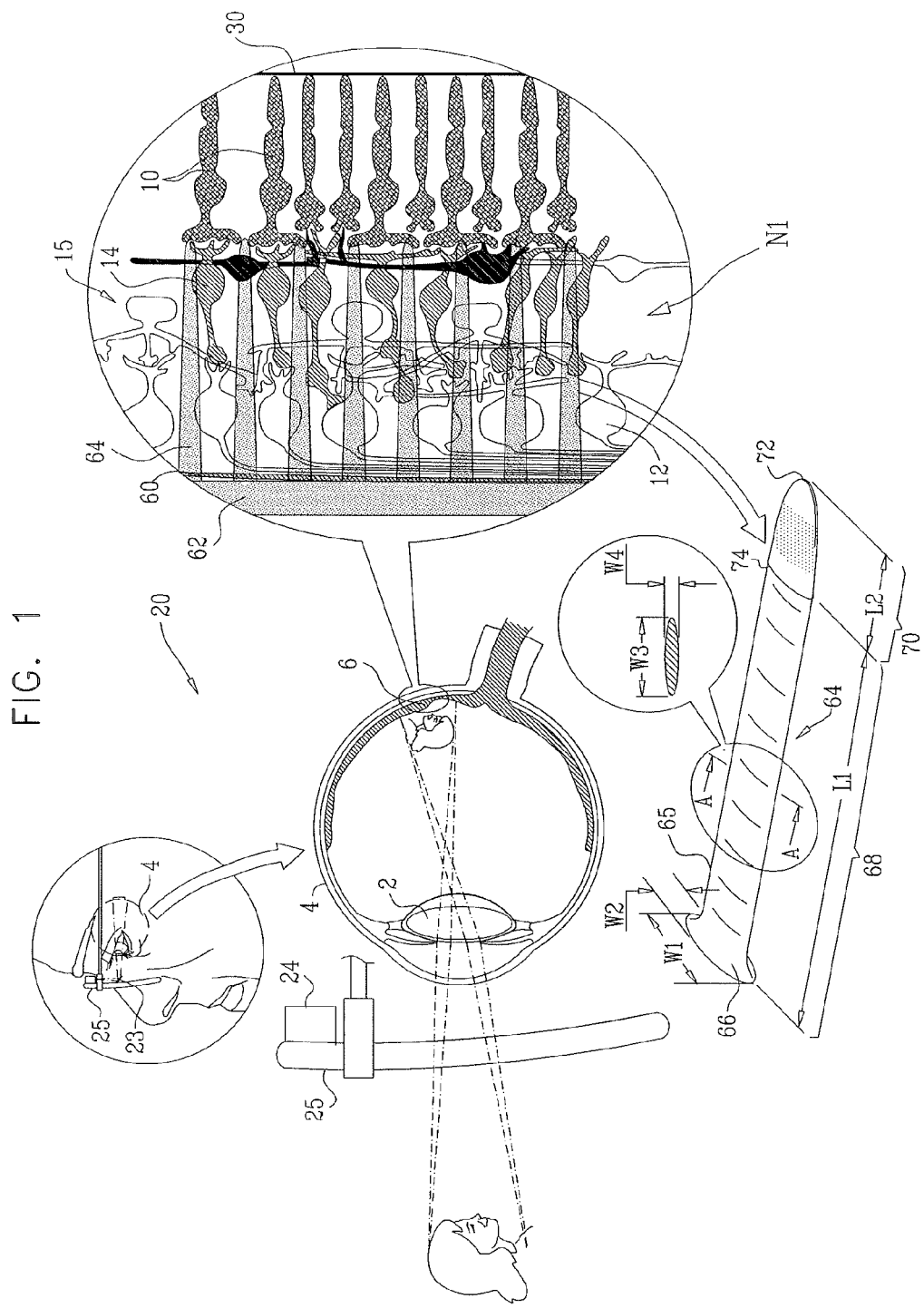
FIG. 1 shows a system for restoring at least partial vision in a subject in accordance with some applications of the present invention.

FIG. 1 shows a system 20 for restoring at least partial vision in a subject, a portion of which is implanted in an eye of the subject, in accordance with some applications of the present invention.

Vision is initiated when light reflecting from objects is focused by lens 2 of eye 4 onto the retina 6. FIG. 1 shows a cross section of a portion of a human retina. The retina is approximately 0.2-0.5 mm thick and lines the back of the eye. As shown, the retina consists of three layers of neurons: photoreceptor cells 10, ganglion cells 12 and many interneurons 15 packed into the central part of the section of retina intervening between the photoreceptors and the ganglion cells. The ganglion cells, which transmit visual information to the brain, lie innermost (as used herein) in the retina, i.e., on the side of the retina closest to the lens and front of the eye. The photoreceptor cells (e.g., rods and cones), which capture light and convert light signals into neural signals, lie outermost in the retina. The central part of the section of retina located between the photoreceptors and the ganglion cells includes the inner nuclear layer (INL), which is made up of bipolar cells 14 and other cells.

The bipolar cell layer typically transmits signals from the photoreceptors 10 to the ganglion cells 12. The rod and cone photoreceptors transfer a signal to the bipolar cells that lay adjacent to the photoreceptor layer. The bipolar cell layer then transmits the signal to the ganglion cells whose axons form the optic nerve. The bipolar cell layer 14 is generally located in a region of the retina that is approximately 130 um-200 um from the inner limiting membrane (ILM), which is the boundary between the vitreous humor in the posterior chamber and the retina itself.

As shown in FIG. 1, for some applications, intraocular apparatus 60 is implanted in an epi-retinal position, typically coupled to the ILM. As described in Zrenner, 2002, which is incorporated herein by reference, epi-retinal arrays are typically implanted onto the retinal surface that separates the retinal neural layer from the vitreous body of the eye's posterior chamber, such that the implant is typically located outside of the vitreous body, contacting the ILM. As appropriate, techniques described in one or more of these references may be adapted for use in implanting apparatus 60.

For some applications, apparatus 60 is implanted in a subretinal position (not shown). As described in Zrenner, 2002, which is incorporated herein by reference, sub-retinal arrays are typically implanted between the pigment epithelial layer 30 and the layer of the retina which contains the photoreceptor cells.

As provided by some applications of the present invention, apparatus 60 comprises a support substrate 62 and a plurality of electrodes 64 protruding from the support substrate. For some applications support substrate 62 comprises components of an intraocular retinal prosthesis. For example, support substrate 62 may comprise an energy receiving layer, a photosensor layer and driving circuitry. The driving circuitry is powered by the energy receiving layer, which typically receives energy from an external device comprising an external power source 24 (e.g., a laser coupled to the frame of a pair of eyeglasses 25, and/or an RF energy source, and/or a magnetic energy source). For some applications a partially-transparent (e.g., half-silvered) mirror 23 is coupled to eyeglasses 25, providing ophthalmoscope functionality to the external device. It is to be noted that for some applications, techniques and apparatus described in U.S. patent application Ser. No. 12/368,150 to Gross et al., entitled, "Retinal Prosthesis," filed Feb. 9, 2009, which issued as U.S. Pat. No. 8,15,526 to Gross et al.,with reference to the external device including the partially transparent mirror, are combined with techniques and apparatus described herein.

The driving circuitry drives electrodes 64 to apply currents to the retina, in response to sensing by the photosensor layer, in order to stimulate the retina 6. Accordingly, system 20 for restoring vision in a subject does not comprise an extraocular camera, and apparatus 60 does not receive image data from outside the eye, but rather utilizes the intact optics and processing mechanisms of the eye 4.

Apparatus 60 typically comprises approximately N1 number of electrodes e.g., 500-6000, e.g, 1000-4000, typically 1600 electrodes 64. For some applications, the electrodes protrude perpendicularly at least 50 um from the support substrate.

Each electrode is typically 100-1000 um in length e.g., 300-600 um, for example, 400 um, in order to reach the outer plexiform layer (OPL), where connections between the bipolar cell layer and the adjacent photoreceptor layer occur. For some applications, each electrode comprises an electrically-insulated body portion 68 coupled to an electrically exposed tip portion 70. Insulated portion 68 of the electrode has a length L1 of between 100 um and 650 um, e.g., 150 um. Exposed tip 70 of electrode 64 typically has a length L2 of between 25 um and 100 um, e.g., 50 um. Typically, electrode 64 has an exposed area of 750 um2. The electrodes 64 protrude from support substrate 62, such that when apparatus 60 is implanted in an eye of a subject, electrodes 64 penetrate tissue of retina 6 and exposed tip portions 70 are typically disposed in bipolar layer 14. Other dimensions of the electrodes are described hereinbelow, with reference to FIGS. 2-3.

FIG. 1 shows a schematic illustration of electrode 64, in accordance with some applications of the present invention. As shown, the insulated portion 68 of electrode 64 includes an elliptical proximal base portion 66 and an elongated body portion 65 extending between the base portion and the exposed tip 70. Tip 70 typically comprises distal tip 72 and tip base 74. Base portion 66 typically has a major axis W1 of between 25 um and 200 um, e.g., 100 um, and a minor axis W2 that is typically 10-100 um, e.g., 50 um. Base portion 66 typically has a larger average diameter than body portion 65, contributing to the structural strength of electrode 64. Body portion 65 is typically generally elliptical, and has a major axis W3 of between 15 um and 60 um, e.g., 30 um, and a minor axis W4 between 5 um and 20 um, e.g., 10 um. Typically, electrodes 64 have a cross-section of 50-200 um2, 20 um from distal tip 72. For some applications electrodes 64 have a cross-section of at least 200 um2, 20 um from distal tip 72.

For some applications, each electrode 64 is typically 25-100 um in length e.g., 50 um, in order to penetrate the nerve fiber layer (NFL) and reach the ganglion cell layer (GCL) 12. Contacting the ganglion cells by electrodes 64 typically enables the use of a reduced amount of power in order to stimulate the ganglion cells. Close proximity to ganglion cells 12 generally results in more focused stimulation that enables higher pixel density for a given amount of current.

Figure 2A:
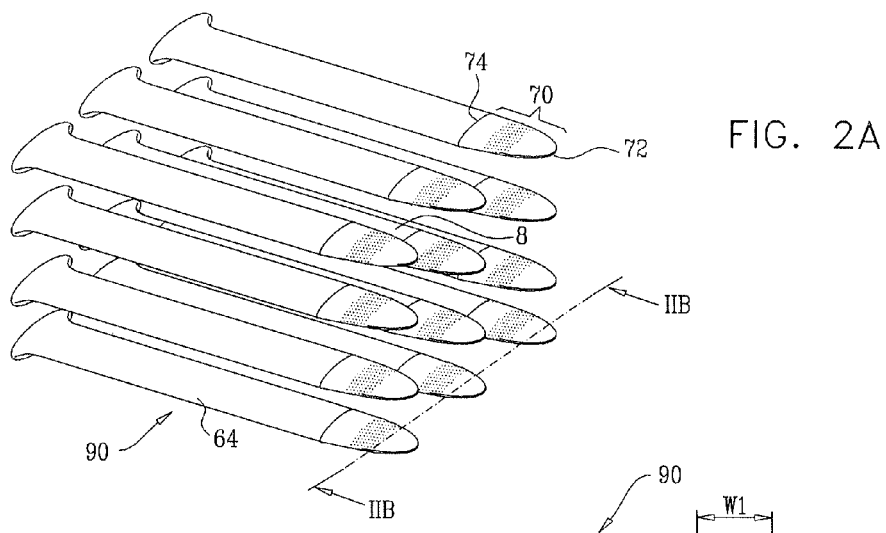
FIGS. 2A-B are schematic illustrations of an array of penetrating electrodes, in accordance with some applications of the present invention.

Reference is made to FIG. 2A, which is a schematic illustration of an array 90 of electrode 64, in accordance with some applications of the present invention. Tip portions 70 of electrodes 64 are typically shaped to define a plurality of perforations passing therethrough. In some applications, tips 70 are generally pointed, to facilitate tissue penetration. The perforated configuration of the tip allows for neuronal processes to intertwine with the electrode tips when electrodes 64 are disposed in retinal tissue of a subject. Increased and direct contact between the electrodes and the neuronal processes, improves the interaction between the neurons, e.g., bipolar cells, and the electrodes. Improved neuron/electrode interaction and coupling enhances stimulation of the neurons by the electrodes. Each tip 70 is typically shaped to define between 1 and 50 perforations (e.g., 1-10) passing therethrough. For some applications, the perforations of each electrode are located 5-20 um (e.g., 10 um) from distal tip 72 and 10-30 um from tip-base 74.

Typically, a spatial density of the perforations of each pointed tip is 0.001-0.02 perforations/um2, or 0.02 to 0.5 perforations /um2, e.g., 0.1 perforations /um2. For some applications, each perforation has a diameter of 1-10 um. The diameter of the perforations in electrode 64 allows axons of bipolar cells, which typically have an average diameter of 1 um, to penetrate and grow through the perforations.

As mentioned hereinabove, for some applications electrodes 64 are disposed in the ganglion cell layer (GCL). In such applications, the axons of the ganglion cells grow through the perforations in electrode tips 70, increasing coupling between the neuronal processes and electrodes 64, and improving stimulation of the ganglion cell layer.

The average diameter of the perforations is typically smaller than the average diameter of a retinal glial cell, which is typically larger than 10 um, preventing glial cells from passing through the perforations in the electrode. Preventing glial cells from passing through the perforations reduces glial encapsulation of the electrodes, and prolongs electrode function.

The perforations are typically created by use of chemical treatments e.g., etching and/or a laser beam. For some applications, the same treatment is used to create the perforations and to increase surface roughness. For some applications, a surface of tip 70 of electrode 64 is coated with carbon nanotubes, attracting neuronal processes to the perforations in tip 70 and increasing adhesion of the neuronal processes to the perforations. Typically, the carbon nanotube coating within the perforation can withstand penetration of neuronal processes into the perforations.

Figure 2B:
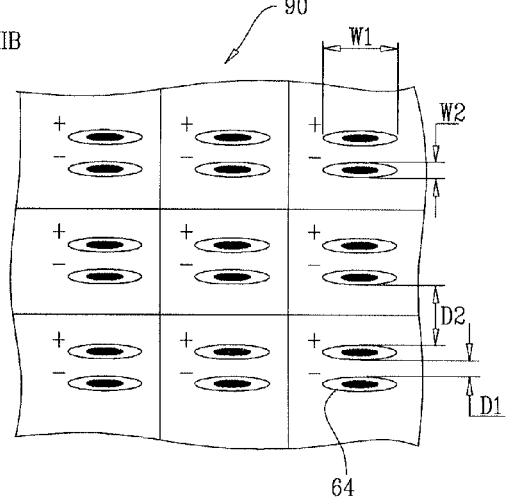

Reference is made to FIG. 2B, which a schematic illustration of an end view of array 90 of electrodes 64, in accordance with some applications of the present invention. Apparatus 60 typically comprises array 90 of electrodes 64 comprising at least 40 electrodes per mm2, e.g., between 100 and 400 electrodes per mm2. FIG. 2B shows array 90 divided into nine units by way of illustration and not limitation. For some applications, each unit is 100 um×100 um in size. Each unit typically comprises a pair of bipolar electrodes. For some applications, both bipolar electrodes (+ and −) in each unit protrude from array 90 and are configured to penetrate tissue of retina 6. One of these electrodes may be stimulating, and the other a return electrode, or else both may be stimulating. For some applications, the stimulating electrode is longer than the return electrode in each pair, and reaches the bipolar layer, while the shorter return electrode only reaches the NFL layer. For other applications, one electrode (either the + or the −) protrudes from array 90 and is configured to penetrate tissue of retina 6, and the other electrode, of opposite polarity, is a surface electrode that is not configured to penetrate tissue of retina 6, but rather functions as a return electrode. The distance D1 between the pair of bipolar electrodes 64 in each unit is typically between 5 and 50 um, e.g., 10 um. The distance D2 between electrodes of adjacent units is typically between 25-100 um, e.g., 50 um. Generally, the distance D1 between a pair of electrodes in each unit is smaller than (e.g., less than half of) the distance D2 between electrodes of adjacent units.

Reference is made to FIGS. 1 and 2A-B. As shown in FIG. 2B, which is a Z view from the distal tip 72 of electrodes 64, the major axis W1 of base portion 66 of insulated portion 68 is typically 1.5-2.5 (e.g., 2) times larger than the minor axis W2 of body portion 65. Typically, major axis W1 is 25-200 um, e.g., 50-150 um (e.g., 100 um), and minor axis W2 is 10-100 um, e.g., 20-80 um (e.g., 50 um)

Reference is again made to FIGS. 1 and 2A-B. As mentioned hereinabove, for some applications, electrodes 64 comprise bipolar electrodes that are configured to penetrate retinal tissue of a subject. Penetrating bipolar electrodes, which are typically implanted such that both the stimulating and return electrodes are in close proximity to a neuronal retinal cell, require a smaller potential between the electrodes and enable reaching a higher potential drop across a given cell, resulting in enhanced stimulation of the cell. This is in contrast to many epi-retinal implants known in the art in which neuronal cells of the retina are stimulated by a surface electrode on the ILM layer.

For some applications, an array 90 of electrodes 64 is divided into clusters of electrodes 64. For such applications, a cluster of three or more, e.g., 3-6, stimulating electrodes, by way of illustration and not limitation, surround and share a common return electrode 8. Each electrode in the cluster receives a signal, through driving circuitry, from a discrete, respective, photosensor in support substrate 62, and in response, stimulates the retina of the subject. In such applications, the return electrode typically has a sufficiently large surface area in order to accommodate the electric current returning from the cluster of stimulating electrodes. Generally, such an arrangement of array of electrodes 64 enables the use of a reduced number of electrodes, since several stimulating electrodes share a common return electrode. For some applications, the stimulating electrodes are configured to drive currents into the cells of retina in alternating time periods. Such staggering of the driving of each electrode in the cluster reduces the amount of return electric current that is driven through the return electrode at a given time. For some applications, array 90 comprises at least 10 clusters of electrodes, e.g., 100-500 clusters. For some applications, array 90 comprises 500-1500 clusters of electrodes.

Figure 8:
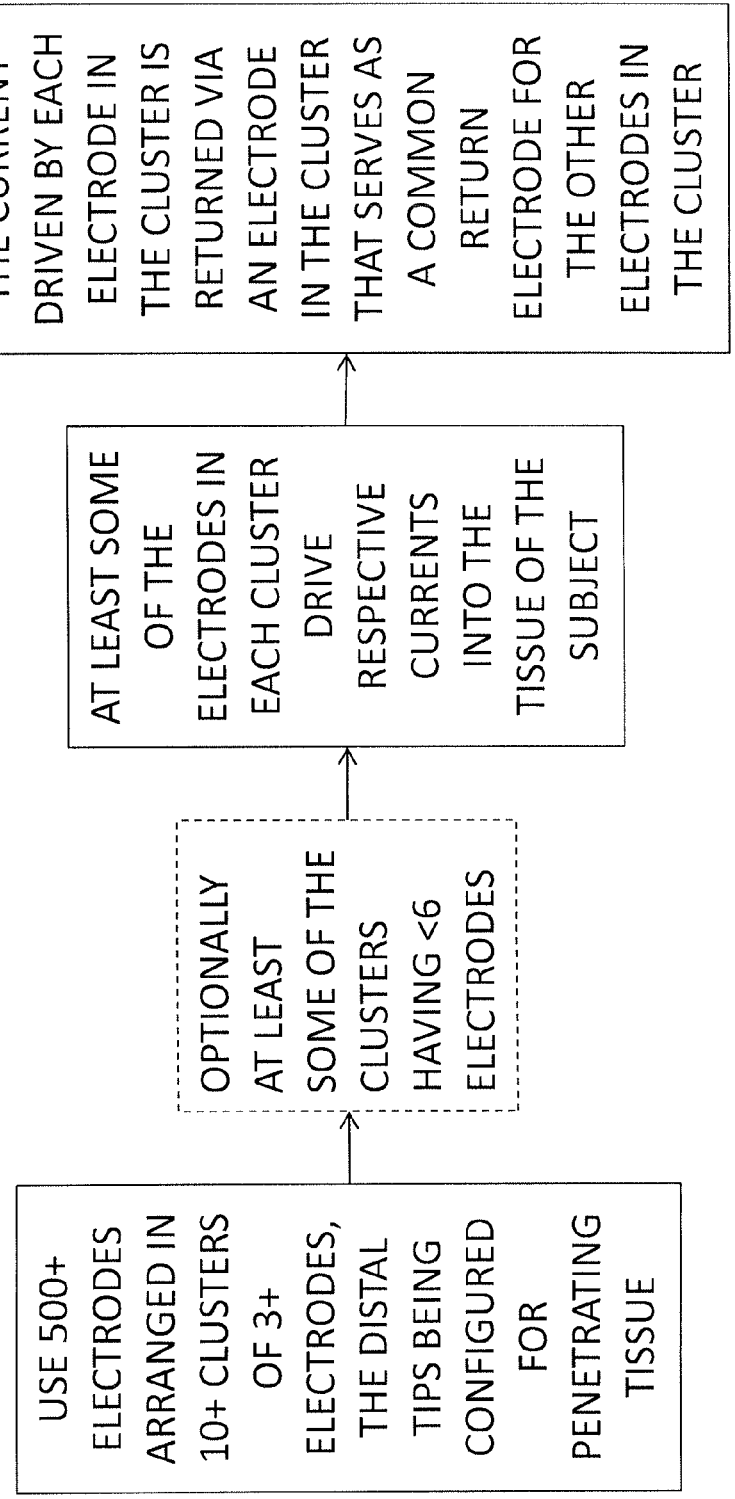
FIG. 8 is a flow chart illustrating a method, in accordance with some applications of the present invention.

Reference is made to FIGS. 2A and 8. FIG. 8 is a flow chart illustrating a method, in accordance with some applications of the present invention. For some applications, at least 500 electrodes protrude at least 50 um from a support substrate, each electrode having (a) a distal tip, (b) an electrically-exposed tip portion, and (c) a cross-section of 50-1500 um2, 20 um from the distal tip. In some applications, the at least 500 electrodes are arranged in at least 10 clusters of three or more electrodes, the distal tips being configured for penetrating tissue of the subject. At least some of the electrodes in each cluster are configured to drive respective currents into the tissue of the subject. The current driven by each electrode in the cluster is returned via an electrode in the cluster that serves as a common return electrode for the other electrodes in the cluster. In some applications, at least some of the clusters include fewer than six electrodes.

Reference is again made to FIGS. 2A-B. Electrodes 64 are typically fabricated by conventional fabrication processes known in the art. For some applications, following fabrication, electrodes 64 are assembled on array 90 by methods such as "pick and place." For other applications, other methods are used to fabricate array 90 of electrodes 64, e.g., three dimensional etching and/or MEMS Palladium etching technique. For some applications, techniques described in one or more of the following patents are practiced in combination with techniques and apparatus described herein: U.S. Pat. Nos. 7,096,568, 6,678,458, 6,923,669, 6,473,365, 6,762,116, 7,025,619, 7,081,630 and U.S. Pat. No. 6,677,225 which are incorporated herein by reference.

Figure 3:
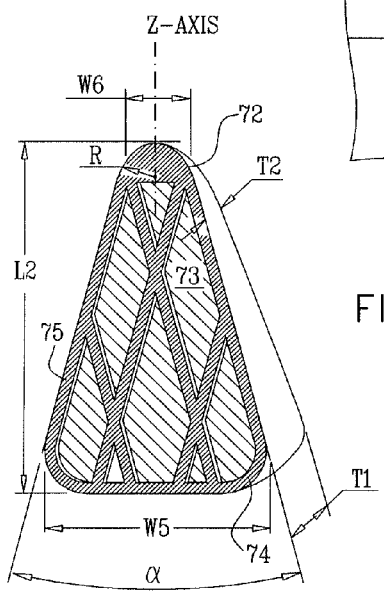
FIG. 3 is a schematic cross-sectional illustration of a pointed tip an of electrode, in accordance with some applications of the present invention.

Reference is now made to FIG. 3, which is a schematic cross-sectional illustration of a tip portion 70, in accordance with some applications of the present invention. Apparatus 60 comprises electrodes which, for some applications, are shaped to define respective pointed tips configured for penetrating tissue of the subject. Each tip 70 is typically an electrically exposed tip, configured to directly drive current into the retinal tissue, e.g., bipolar cell layer, causing stimulation of the tissue and resulting in enhanced vision. Exposed tip 70 of the electrode typically has a length L2 of between 25 um and 100 um, e.g., 50 um. Typically, although each tip 70 is pointed when viewed from a distance, and thus functions as a pointed tip for purposes such as penetrating tissue, a close examination of the tip 70 reveals that it is shaped to have a radius of curvature R of 0.5-10 um, e.g., 2 um.

Tip 70 may be shaped to define a tip having an angle alpha of 30-60 degrees. As shown in FIG. 3, tip 70 comprises a tip-base portion 74 and a distal tip 72. Base portion 74 of tip 70, which is at a distal end of the electrode body portion, has a width W5 of between 15 um and 60 um, e.g., 30 um. Tip 70 typically decreases monotonically in width along its longitudinal axis from tip-base portion 74 to distal tip 72, until it reaches a width W6 of between 1 um and 20 um, e.g., 10 um, 4 um proximal from distal tip-end 72. For some applications, tip 70 is reduced in size after electrode shaping by techniques such as laser ablation.

As shown in FIG. 3, tip 70 typically decreases monotonically in thickness along its longitudinal axis from base portion 74 to distal tip 72. Base portion 74 of tip 70 has a thickness T1 of between 5 um and 20 um, e.g., 10 um. Distal tip 72 of tip 70 has a thickness T2 of between 0.5 um and 5 um, e.g., 2 um. The shape of the distal tip of tip 70, and a radius of curvature R of tip 70, typically reduces the extent to which tip 70 penetrates and/or ruptures cells with which it comes in contact. Typically, retinal neuronal cells range between 5 and 10 um. Radius of curvature R is typically 0.5 um-10 um, e.g., 2 um, roughly in the same magnitude as the cells. Generally, all edges of electrode tip 70 and electrode 64 have a radius of curvature that is greater than 0.1 um, e.g., greater than 0.5 um. Rounding of the edges is typically done to reduce concentration of charge at sharp edges. Surface treatments to increase roughness of a surface of tip 70, as described hereinbelow, are also used to smoothen and round edges of tip 70 and electrode 64.

Typically, tip 70 of electrode 64 is treated to increase surface roughness of tip 70. For some applications, an area 73 of tip 70 is treated to increase roughness, whereas another area 75 of tip 70 remains untreated in order to maintain structural strength of the tip.

Reference is made to FIGS. 2A-B and 3. As shown in FIG. 3, untreated areas 75 are maintained in order to strengthen tip 70 for withstanding compression forces applied during penetration of tip 70 into retinal tissue. Surface treatment of the tip in areas 73 typically affects an area of the tip that is as deep as 2 um from the surface. Increased surface roughness causes an increased surface area of the tip. The tip is treated to increase roughness such that 1 mm2 area has an equivalent surface area of between 10 mm2 and 1000 mm2, e.g., 100 mm2. Increased surface area generally reduces electrode impendence, thereby enhancing stimulation of retinal tissue by electrodes 64. Additionally, increased roughness generally reduces surface charge density and improves electrode capacitance, enabling an increase in the charge injection limit. Increased surface roughness to reduce charge density is typically achieved by techniques of nanofabrication and/or metal etching, as described in Lianga, 2008 (referenced hereinabove).

For some applications, electrodes 64 are coated with carbon nanotubes. Typically, carbon nanotubes create a rough surface in electrode 64, including tip portion 70. Rough surfaces in general and carbon nanotube surfaces in particular have been shown to attract neurons and promote neuronal growth. As described in Sorkin et al., 2009 (referenced above) neurons were found to bind and preferentially anchor to carbon nanotube rough surfaces. Thus, adhesion of retinal neurons, e.g., bipolar cells, to carbon nanotube electrodes provided by these applications of the present invention, promotes cell-electrode coupling and/or axon regeneration, leading to improved stimulation of the retina. For some applications, the carbon nanotube coating of electrode 64 is glued to the electrode surface and/or grown on a selected surface of the electrode by using doping techniques known in the art.

For some applications, a femtosecond laser is used to increase surface roughness of electrodes 64. Femtosecond laser treatment produces rough surface structures on titanium possibly for the use of implants and other biomedical applications treatments (Vorobyev et al., 2007). As described in Vorobyev et al., 2007 (referenced above) femtosecond laser treatment increases the roughness of a titanium substrate in the range of 1-15 um. Additionally, femtosecond laser treatment was shown to produce a variety of surface nanostructures, such as nanoprotrusions and nanopores on the titanium substrate. Liang et al., 2007, (referenced above), report good bioactivity of a pure titanium substrate that was treated with a femtosecond laser to increase roughness of its surface.

For some application, a blanket etch MEMS procedure is used to increase surface roughness of electrodes 64. For such applications, the entire electrode 64 is blanketed and tip 70 is etched to increase surface roughness and achieve a desired aspect ratio in a similar procedure to that described in U.S. Pat. No. 6,770,521 to Visokay.

Reference is made to FIGS. 4A-B, which are schematic illustration of intraocular apparatus 60, in accordance with some applications of the present invention. Apparatus 60 typically comprises an array 1090 of protruding electrodes 1064 configured to penetrate the retina of a subject. It is to be noted that techniques and apparatus described hereinabove with reference to electrodes 64 and array 90 apply to electrodes 1064 and array 1090, except where otherwise indicated. For some applications, electrodes 1064 vary in length. Electrodes 61 are generally longer than electrodes 62, thereby facilitating direct stimulation of distinct areas of the retina, e.g., the bipolar layer and/or the ganglion cell layer. Other dimensions of the electrodes are described hereinbelow, with reference to FIG. 6.

Electrodes 1064 comprise any suitable material e.g., palladium and/or titanium, and/or silicon electrodes. For some applications, electrodes 1064 comprise a metal alloy and/or doped electrodes. Typically, a silicon wafer 1030 forms the base of array 1090 from which electrodes 1064 protrude. For some applications, wafer 1030 is selectively etched to a desired depth by using any suitable technique known in the art, e.g., techniques of Deep Reactive Ion Etching (DRIE). For some applications, following bonding of the silicon wafer, electrodes 1064 are etched by using any suitable technique known in the art, e.g., techniques of Deep Reactive Ion Etching (DRIE), to have desired dimensions and aspect ratios. For some applications, additional metals such as platinum, and/or palladium, are deposited on electrodes 1064 by using, for example, a shadow mask technique. An attaching titanium ring frame 1020 is typically electroplated with electrodes 1064 to form structure that can subsequently be welded to the metal ring case 2020 (shown in FIG. 5). The silicon wafer 1030 is typically biocompatible. Ring frame 1020 is typically bonded to silicon wafer 1030, by using, e.g., fusion bonding. Suitable fusion bonding techniques are described in an article by Jourdain et al., entitled, "Fabrication of piezoelectric thick-film bimorph micro-actuators from bulk ceramics using batch-scale methods," which is incorporated herein by reference. Wafer 1030 typically comprises through-wafer vias.

Typically, apparatus 60 additionally comprises a CMOS chip 1040 including through-silicon vias. For some applications, solder bumps 1050 are deposited on an upper side of CMOS chip 1040, electrically connecting chip 1040 to silicon wafer 1030. Additionally, for some applications, apparatus 60 comprises a layer 1060. Layer 1060 typically comprises additional elements of an intraocular retinal prosthesis, e.g., an energy receiving layer, a photosensor layer and driving circuitry that is powered by the energy receiving layer. The driving circuitry typically drives current into the retinal tissue from the rough tips 1070 of electrodes 1064, in response to sensing by the photosensor layer, in order to stimulate the retinal tissue. The electrical signal generated by layer 1060 is typically routed through silicon wafer 1030 to electrodes 1064, providing sealing on one side and electrical contact on the other.

For some applications, a back side of the titanium wafer is bound to a glass cap 80 which, as shown in FIG. 4B, encapsulates the entirety of apparatus 60, excluding array 1090 of protruding electrodes 1064. For some applications, glass cap 80 comprises two distinct glass pieces, one of which is shaped to define a hole. The glass pieces are typically bonded to each other by anodic bonding, forming a single glass cap 80. Bonding of titanium frame 1020 to glass cap 80 is optionally done using thermal compression bonding. This low temperature bonding step generally does not affect circuitry of apparatus 60. Glass cap 80 generally reduces exposure of human tissue to any toxic materials, e.g., contaminated silicon, which may exist in apparatus 60. Typically, laser welding is used to close the glass encapsulation.

Reference is made to FIG. 5, which is a schematic illustration of apparatus 60, in accordance with some applications of the present invention. As described hereinabove, apparatus 60 typically comprises array 1090 of electrodes 1064, which are configured to penetrate retinal tissue of a subject. For some applications, electrodes 1064 comprise long electrodes 61 and short electrodes 62. Array 1090 is typically bonded to silicon wafer 1030 which is coupled to CMOS chip 1040 via solder bumps 1050. As shown in FIG. 5, for some applications, apparatus 60 comprises a metal ring 2020 which encapsulates the entirety of apparatus 60, excluding array 1090 of protruding electrodes 1064.

Reference is now made to FIGS. 1 and 5. As described hereinabove with reference to FIG. 1, each electrode in apparatus 60 comprises an electrically-insulated body portion coupled to an electrically exposed distal tip. FIG. 5 shows an exploded view of electrodes 1064 showing body portion 1068 of electrodes 1064 coated with a polyimide insulating coating 82. Tip 1070 of electrode 1064 remains electrically exposed, i.e., not coated with a polyimide coating, to enable an electrical connection between the tip and the bipolar layer (or other portions of the retina). As described hereinabove, in some applications, tip 1070 physically contacts the bipolar layer when apparatus 60 is implanted in the eye of a subject. For some applications, the entire electrode is fabricated to include a polyimide coating, followed by for example, an etching process to selectively remove the polyimide coating from electrode tip 1070. Alternatively, the polyimide coating is removed from the tip 70 by laser ablation. Seo et al. (2004) (referenced hereinabove) report that polyimide is a suitable material for a retinal prosthesis.

As described hereinabove with reference to FIG. 3, the electrically exposed tips of the electrodes are treated to increase surface roughness. Accordingly, FIG. 5 shows tip 1070 having a rough surface to increase neuronal cell adhesion to tip 1070, thus increasing tissue stimulation by electrodes 1064. Typically, tip 1070 is configured to penetrate retinal tissue of a subject.

Typically, apparatus 60 is configured to match the natural curvature of the retina to facilitate implantation and anchoring of apparatus 60 to the retina. Accordingly, electrodes 1064 typically vary in length, and as indicated by FIGS. 4A-B and 5, for some applications, tips 1070 of electrodes 1064 together define a convex curved surface having a radius of curvature that is 6-15 mm.

Figure 6:
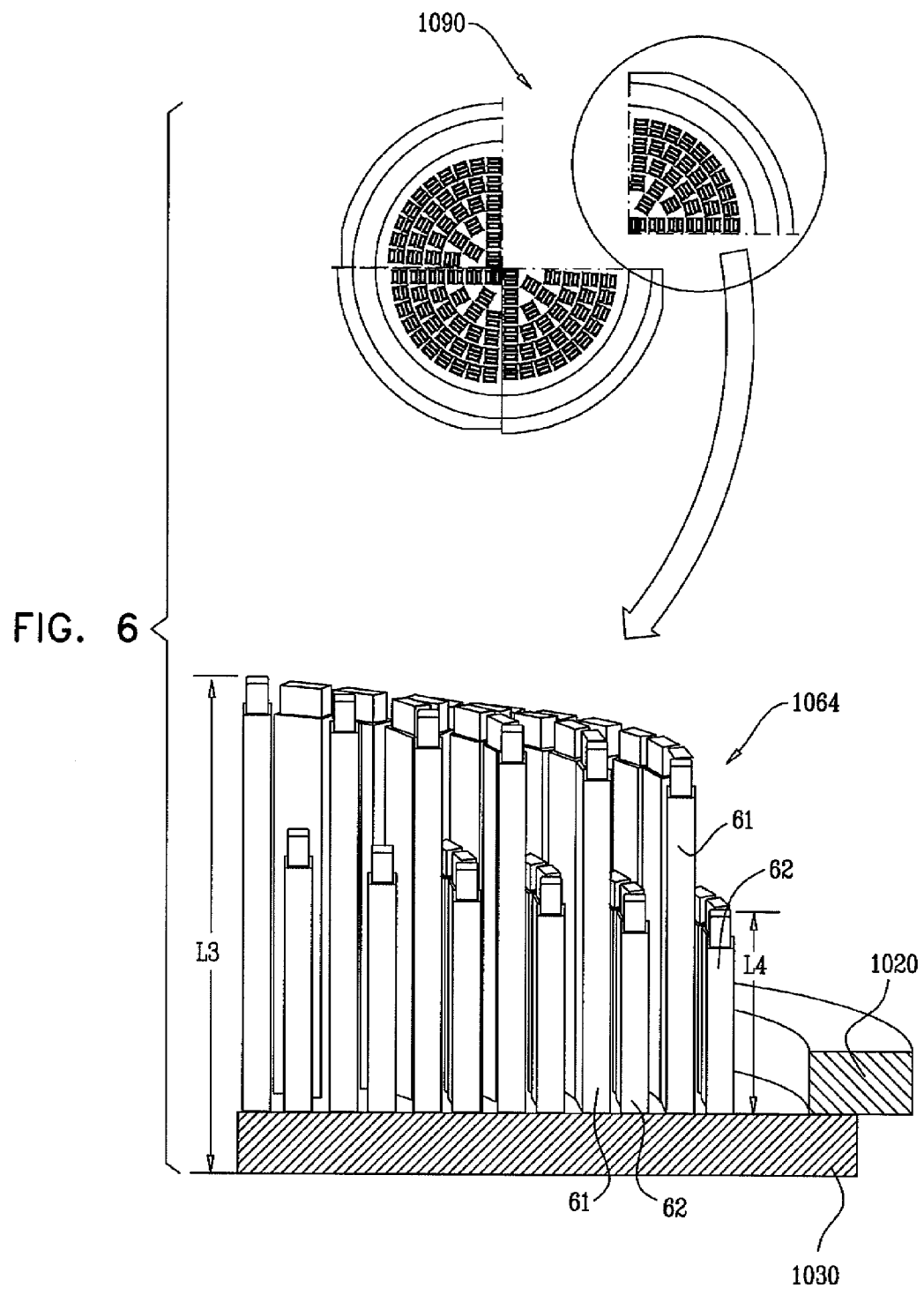
FIG. 6 is a schematic illustration of an array of penetrating electrodes, in accordance with some applications of the present invention.

Reference is made to FIG. 6 which is a schematic illustration of a section of array 1090 of electrodes 1064, in accordance with some applications of the present invention. As shown, array 1090 typically comprises electrodes 1064 of varying heights. For some applications, electrodes 1064 are arranged in concentric circles on wafer 1030. The circles of electrodes 1064 typically alternate between long electrodes 61 and short electrodes 62, such that electrodes 1064 are typically arranged in pairs of bipolar electrodes. Each pair of electrodes typically comprises a single long electrode 61 and a single short electrode 62.

Apparatus 60 and electrodes 1064 are typically configured to match the natural curvature of a human organ and/or tissue in which it is implanted, e.g., the retina. As shown in FIG. 6, for some applications, electrodes 1064 vary in length. Electrodes 61 are generally longer than the electrodes 62, thereby facilitating direct stimulation of distinct areas of the retina, e.g., the bipolar layer and/or the ganglion cell layer. For some applications, long electrodes 61 have a length L3 of 200-800 um, e.g., 300-500. Short electrodes 62 typically have a length L4 of 100-550 um, e.g., 150-350. Typically long electrodes 61 are 50-150 um longer than the adjacent short electrodes 62. For some applications, both long electrodes 61 and short electrodes 62 function as stimulating electrodes. For other applications, long electrodes 61 function as stimulating electrodes and short electrodes 62 function as return electrodes. For some applications, return electrodes 62 are less than 10 um in length, and may even comprise surface electrodes. In this case, L4 is less than 5 um in length.

Figure 7:
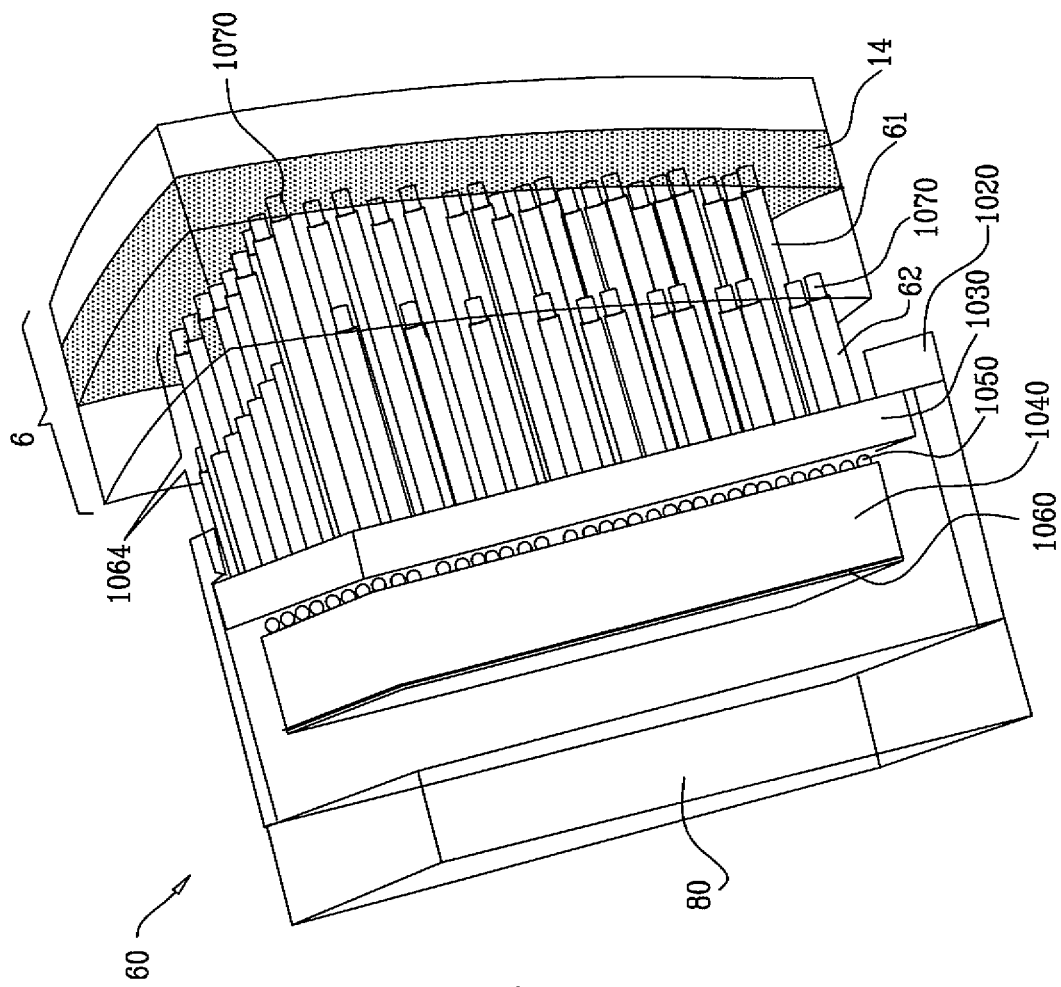
FIG. 7 is a schematic illustration of intraocular apparatus penetrating retinal tissue, in accordance with some applications of the present invention.

Reference is made to FIG. 7, which is a schematic illustration of apparatus 60 disposed in retina 6, in accordance with some applications of the present invention. FIG. 7 shows components of apparatus 60 (silicon wafer 1030, attaching ring frame 1020, CMOS chip 1040, solder bumps 1050 and layer 1060) in glass encapsulation 80. Electrodes 1064 are shown penetrating retina 6. For some applications, and as described hereinabove with reference to FIG. 6, electrodes 1064 of apparatus 60 are arranged in pairs of bipolar electrodes. For some applications, both bipolar electrodes (+ and −) of each pair protrude from apparatus 60, and are configured to penetrate tissue of retina 6. For some applications, the electrodes in each pair are of varying lengths, such that one electrode (either the + or the −) is longer than the second electrode. Typically, the longer electrode 61 (e.g., 200-800 um in length) is configured to protrude from apparatus 60 and penetrate retinal tissue in order to contact and stimulate the bipolar cell layer. The shorter electrode 62 (e.g., 100-550 um in length) is typically configured to protrude from apparatus 60 in order to contact and stimulate epi-retinal tissue, e.g., the NFL layer. Additionally or alternatively, short electrode 62 is configured to penetrate and stimulate retinal ganglion cells. For some applications, long electrodes 61 function as stimulating electrodes, e.g., to stimulate the bipolar layer and short electrodes 62 function as return electrodes.

For other applications, one electrode (either the + or the −) protrudes from apparatus 60 and is configured to penetrate tissue of retina 6, and the other electrode, of opposite polarity, is a surface electrode that is not configured to penetrate tissue of retina 6, but rather functions as a return electrode (application not shown). Typically, apparatus 60 comprises at least 100 short or surface electrodes, and at least 400 long electrodes.

For some applications, electrodes 1064 comprise hook electrodes configured to anchor to retinal tissue of a subject, increasing coupling between the target cells and the electrode.

Reference is made to FIGS. 1-7. For some applications, apparatus 60, including substrate 62, is flexible and can be adjusted to match the natural curvature of the retina during implantation. Apparatus 60 may be adjusted to match the retina of a subject by standard fitting and/or can be tailor made according to OCT imaging of the retina. Once adjusted to match the natural curvature of the retina, apparatus 60 is typically glued and/or stitched in place. For other applications, apparatus 60 is generally rigid, and electrodes of varying heights and, optionally, shapes enable proper attachment of the apparatus to the curved structure of the retina.

Reference is again made to FIGS. 1-7. It is to be noted that a plurality of implantable apparatuses 60 may be implanted in discrete locations in tissue of retina 6, either arranged in an array, or, for example, pseudo-randomly. Typically, apparatus 60 is wireless and does not comprise bulky components, facilitating implantation of several implants 60 in retina 6 of the subject.

It is to be noted that a system comprising penetrating electrodes with rough and/or perforated tips as described hereinabove with reference to FIGS. 1-7, may be implanted in any other organ (e.g., brain, nose, ears and/or tongue), and used in any other neurological application (e.g., cortex stimulation). Implantation of penetrating electrodes as described hereinabove in, for example, brain tissue of a subject typically reduces the amount of power required to stimulate the tissue. Additionally or alternatively, implantation of such electrodes facilitates specific sensing and enhances specific stimulation of a target neuron in the tissue by directly contacting selective areas with the electrodes.

For some applications, a system comprising penetrating electrodes as described hereinabove may be used to stimulate organs such as the liver or the pancreas. Implanting an array of such electrodes in, for example, selected areas of pancreatic tissue (e.g., insulin-secreting areas) enables specific and more effective stimulation of these areas.

The scope of the present invention includes embodiments described in the following patent application, which is incorporated herein by reference. For some applications, techniques and apparatus described in the following patent application are combined with techniques and apparatus described herein:

U.S. patent application Ser. No. 12/368,150 to Gross, entitled, "Retinal Prosthesis," filed Feb. 9, 2009 and published as U.S. Patent Application Publication 2010/0204754 to Gross et al., and, which issued as U.S. Pat. No. 8,150,526 to Gross et al.

For some applications, techniques described herein are practiced in combination with techniques described in one or more of the references cited in the Background section of the present patent application, which are incorporated herein by reference.

It will be appreciated by persons skilled in the art that the present invention is not limited to what has been particularly shown and described hereinabove. Rather, the scope of the present invention includes both combinations and subcombinations of the various features described hereinabove, as well as variations and modifications thereof that are not in the prior art, which would occur to persons skilled in the art upon reading the foregoing description.

The invention claimed is:

1. An apparatus configured for implantation in a body of a subject, comprising:
   a support substrate; and
   at least 500 electrodes protruding at least 50 um from the support substrate, each electrode having (a) a distal tip, (b) an electrically-exposed tip portion, (c) an electrically-insulated body portion, proximal to the electrically-exposed tip portion, and (d) a cross-section of 50-200 $um^2$, at a site 20 um from the distal tip,
   wherein the electrically-exposed tip portion of each electrode and the electrically-insulated body portion of each electrode are configured to penetrate retinal tissue of an eye of the subject, and
   wherein each electrode is less than 600 um in length.

2. The apparatus according to claim 1, wherein each electrode tip has a rough surface.

3. The apparatus according to claim 1, wherein the retinal tissue of the subject includes a retinal bipolar cell layer of the subject, and wherein the tips are configured to penetrate the retinal bipolar cell layer.

4. The apparatus according to claim 1, wherein the tissue of the subject includes a retinal ganglion cell layer of the subject, and wherein the tips are configured to penetrate the retinal ganglion cell layer.

5. The apparatus according to claim 1, wherein the electrically-exposed tip portion of each electrode is 50-100 um in length.

6. The apparatus according to claim 1, wherein each distal tip has a radius of curvature of 0.5-5 um.

7. The apparatus according to claim 1, wherein the radius of curvature of the distal tips is 1-3 um.

8. The apparatus according to claim 1, wherein a distance from the substrate to the distal tip of each electrode is 200-500 um.

9. The apparatus according to claim 1, wherein the distal tip of the tips of the electrodes have an average distance from the support substrate of 50-150 um.

10. The apparatus according to claim 1, wherein the support substrate is generally flexible.

11. The apparatus according to claim 1, wherein the tips of the electrodes together define a convex curved surface having a radius of curvature that is 6-15 mm.

12. The apparatus according to claim 1, further comprising at least 100 surface electrodes, and wherein the protruding electrodes are shaped to define respective tips having rough surfaces.

13. The apparatus according to claim 12, wherein the surface electrodes are configured to function as return electrodes.

14. The apparatus according to claim 1, wherein the at least 500 electrodes are arranged in at least 10 clusters of three or more electrodes, and wherein:
   at least some of the electrodes in each cluster are configured to drive respective currents into the tissue of the subject, and
   the current driven by each electrode in the cluster is returned via an electrode in the cluster that serves as a common return electrode for the other electrodes in the cluster.

15. The apparatus according to claim 14, wherein at least some of the clusters comprise fewer than six electrodes.

16. The apparatus according to claim 1, wherein a spatial density of the electrodes is 100-400 electrodes per $mm^2$.

17. The apparatus according to claim 1, wherein the electrically-insulated body portion of each electrode has a cross section of 59-942$um^2$, midway along the electrically-insulated body portion of the electrode.

18. The apparatus according to claim 3, wherein the retinal tissue of the subject further includes a retinal ganglion cell layer of the subject, and wherein the electrically-insulated body portion of each electrode is configured to penetrate the retinal ganglion cell layer.

19. A method for retinal stimulation comprising:
   identifying a subject as suffering from a retinal disease;
   in response to identifying the subject, implanting in an eye of the subject an apparatus including:
      a support substrate; and
      at least 500 electrodes protruding at least 50um from the support substrate, each electrode having (a) a distal tip, (b) an electrically-exposed tip portion, (c) an electrically-insulated body portion, proximal to the electrically-exposed tip portion, (d) a length of less than 600 um and (e) a cross-section of 50-200 $um^2$, at a site 20um from the distal tip; and
   positioning the apparatus such that the electrically-exposed tip portion of each electrode and the electrically-insulated body portion of each electrode penetrate retinal tissue of the eye of the subject.

* * * * *